US011267875B2

(12) United States Patent
Wu et al.

(10) Patent No.: US 11,267,875 B2
(45) Date of Patent: Mar. 8, 2022

(54) HUMANIZED ANTI-DKK2 ANTIBODY AND USES THEREOF

(71) Applicant: YALE UNIVERSITY, New Haven, CT (US)

(72) Inventors: Dianqing Wu, Cheshire, CT (US); Bo Chen, Daly City, CA (US); Hai Wu, Palo Alto, CA (US)

(73) Assignee: Yale University, New Haven, CT (US)

( * ) Notice: Subject to any disclaimer, the term of this patent is extended or adjusted under 35 U.S.C. 154(b) by 776 days.

(21) Appl. No.: 15/771,965

(22) PCT Filed: Oct. 20, 2016

(86) PCT No.: PCT/US2016/057814
§ 371 (c)(1),
(2) Date: Apr. 27, 2018

(87) PCT Pub. No.: WO2017/074774
PCT Pub. Date: May 4, 2017

(65) Prior Publication Data
US 2018/0230204 A1    Aug. 16, 2018

Related U.S. Application Data

(60) Provisional application No. 62/247,410, filed on Oct. 28, 2015.

(51) Int. Cl.
| | | |
|---|---|---|
| C07K 16/18 | (2006.01) | |
| C12Q 1/6886 | (2018.01) | |
| C07K 16/28 | (2006.01) | |
| G01N 33/68 | (2006.01) | |
| G01N 33/574 | (2006.01) | |
| A61K 39/395 | (2006.01) | |
| A61K 39/00 | (2006.01) | |
| A61P 35/04 | (2006.01) | |
| A61P 35/00 | (2006.01) | |

(52) U.S. Cl.
CPC ...... *C07K 16/18* (2013.01); *A61K 39/001102* (2018.08); *A61K 39/39558* (2013.01); *A61P 35/00* (2018.01); *A61P 35/04* (2018.01); *C07K 16/2818* (2013.01); *C12Q 1/6886* (2013.01); *G01N 33/574* (2013.01); *G01N 33/68* (2013.01); *A61K 2039/505* (2013.01); *A61K 2039/507* (2013.01); *C07K 2317/24* (2013.01); *C07K 2317/34* (2013.01); *C07K 2317/76* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2006/0294605 A1* | 12/2006 | McCarthy | C12Q 1/6886 800/14 |
| 2007/0128187 A1* | 6/2007 | Allen | C07K 16/30 424/143.1 |
| 2011/0305687 A1 | 12/2011 | Weng et al. | |
| 2014/0170147 A1 | 6/2014 | Shulok et al. | |
| 2014/0193427 A1 | 7/2014 | Lerner et al. | |
| 2014/0314714 A1 | 10/2014 | Honjo et al. | |
| 2018/0162942 A1* | 6/2018 | Simon | C07K 16/2818 |
| 2018/0230204 A1 | 8/2018 | Wu et al. | |

FOREIGN PATENT DOCUMENTS

| | | |
|---|---|---|
| CN | 106659912 A | 5/2017 |
| KR | 20140136593 A | 12/2014 |
| KR | 101508052 B1 | 4/2015 |
| WO | 2012103787 A1 | 8/2012 |
| WO | 2016004055 A1 | 1/2016 |

OTHER PUBLICATIONS

Almagro & Fransson, Frontiers in Bioscience 2008; 13:1619-33.*
De Genst et al., Developmental and Comparative Immunology, 2006, 30:187-98.*
Ward et al. (Nature, 1989, 341:544-546).*
Barthelemy et al. (Journal of Biological Chemistry, 2008, 283:3639-3654).*
Choi et al., 2011, Molecular BioSystems, 2011, 7:3327-334.*
Griffiths et al. (The EMBO Journal, 1993, 12:725-734.*
Klimka et al., British Journal of Cancer, 2000, 83:252-260.*
Beiboer et al. (Journal of Molecular Biology, 2000, 296:833-849.*
Creative Biolabs, "Datasheet: Recombinant Human Anti-DKK2 Antibody (5F8-HXT1-V2)" 2019 < https://www.creativebiolabs.net/pdf/HP AB-0057CQ-F(E).pdf > [retrieved on Apr. 4, 2019].
Creative Biolabs, "Datasheet: Recombinant Human Anti-DKK2 Antibody scFv Fragment (5F8-HXT1-V2)" 2019 < https://www.creativebiolabs.net/pdf/HP AB-0057CQ-S(P).pdf > [retrieved on Apr. 4, 2019].

(Continued)

*Primary Examiner* — Brad Duffy
(74) *Attorney, Agent, or Firm* — Saul Ewing Arnstein & Lehr LLP; Kathryn Doyle; Justin Crotty

(57) ABSTRACT

The present invention relates to the discovery that inhibition of Dickkopf2 (DKK2) increases $CD8^+$ cytotoxic T lymphocyte (CTL) activity, attenuates tumor, and hence suppresses tumor formation. Thus, in various embodiments described herein, the methods of the invention relate to methods of treating cancer by administering to a patient an effective amount of a humanized anti-DKK2 antibody, methods for providing anti-tumor immunity in a subject, methods of stimulating a T cell mediated immune response to a cell population or a tissue and suppressing tumor in a subject. Additionally, the current invention includes methods of diagnosing a cancer or a predisposition of developing a cancer or a metastasis and methods for determining the use of immunotherapy treatment or cancer vaccine for treating cancer. Furthermore, the invention encompasses a pharmaceutical composition for treating cancer as well as a kit for carrying out the aforementioned methods.

6 Claims, 22 Drawing Sheets

Specification includes a Sequence Listing.

(56) References Cited

OTHER PUBLICATIONS

Creative Biolabs, "Datasheet: Recombinant Human Anti-DKK2 Antibody Fab Fragment (5F8-HXT1-V2)" 2019 < https://www.creativebiolabs.net/pdf/HP AB-0057CQ.pdf> [retrieved on Apr. 4, 2019].
Extended European Search Report for European Patent Application No. 16860530.1 dated Apr. 23, 2019.
Uniprot Accession Q9UBU2 ,2016.
Internet Archive-Antigen, Antibodies Online.com ,2015.
Brott, et al.,Regulation of WNT/LRP signaling by distinct domains of Dickkopf proteins, Mol Cell Biol. 22(17) ,2002 ,6100-6110.
Gage, et al.,The canonical Wnt signaling antagonist DKK2 is an essential effector of PITX2 function during normal eye development, Dev Biol. 317(1) ,May 2008 ,310-324.
Guo, et al.,Therapeutic cancer vaccines: past, present, and future, Adv Cancer Res. 119 ,2013 ,421-475.
Hauer, et al.,DKK2 mediates osteolysis, invasiveness, and metastatic spread in Ewing sarcoma, Cancer Res. 73(2) ,2013 ,967-977.
Hirano, et al.,Blockade of B7-H1 and PD-1 by monoclonal antibodies potentiates cancer therapeutic immunity, Cancer Res. 65(3) ,2005 ,1089-1096.
Hirata, et al.,Wnt antagonist gene DKK2 is epigenetically silenced and inhibits renal cancer progression through apoptotic and cell cycle pathways, Clin Cancer Res. 15(18) ,2009 ,5678-5687.
Li, et al.,Dkk2 has a role in terminal osteoblast differentiation and mineralized matrix formation, Nat Genet. 37(9) , Sep. 2005 ,945-952.
Li, et al.,MicroRNA-222 promotes tumorigenesis via targeting DKK2 and activating the Wnt/β-catenin signaling pathway, FEBS Lett. 587(12) ,2013 ,1742-1748.
Li, et al.,Second cysteine-rich domain of Dickkopf-2 activates canonical Wnt signaling pathway via LRP-6 independently of dishevelled, J Biol Chem. 277(8) ,2002 ,5977-5981.
Matsui, et al.,Dickkopf-4 and -2 genes are upregulated in Human Colorectal Cancer, Gastroenterology & 55th Annual Meeting of the Society for the Surgery of the Alimentary Tract (SSAT)/Digestive Disease WE; Chicago, IL, 138(5) ,May 3-6, 2014 ,S-734.
Matsui, et al.,DICKKOPF-4 and -2 genes are upregulated in human colorectal cancer, Cancer Sci.100(10) ,Oct. 2009 ,1923-1930.
Monaghan, et al.,Dickkopf genes are co-ordinately expressed in mesodermal lineages, Mech Dev. 87(1-2) ,1999 ,45-56.
Mukhopadhyay, et al.,Dkk2 plays an essential role in the corneal fate of the ocular surface epithelium, Development 133(11) ,Jun. 2006 ,2149-2154.
Niehrs, et al.,Function and biological roles of the Dickkopf family of Wnt modulators, Oncogene. Dec. 4, 2006;25(57) ,2006 ,7469-7481.
Niida, et al.,DKK1, a negative regulator of Wnt signaling, is a target of the beta-catenin/TCF pathway, Oncogene. 23(52) ,2004 ,8520-8526.
Park, et al., Distinct roles of DKK1 and DKK2 in tumor angiogenesis, Angiogenesis. 17(1) ,2014 ,221-234.
Revet, et al.,MSX induces the Wnt pathway antagonist genes DKK1, DKK2, DKK3, and SFRP1 in neuroblastoma cells, but does not block Wnt3 and Wnt5A signalling to DVL3, Cancer Lett. 289(2) ,Mar. 2010 ,195-207.
Tai, et al.,Targeting the WNT Signaling Pathway in Cancer Therapeutics, Oncologist. Oct. 2015;20(10) ,Oct. 2015 ,1189-1198.
You, et al.,Developmental abnormalities in multiple proliferative tissues of Apc(Min/+) mice, Int J Exp Pathol. 87(3) ,2006 ,227-236.
Zhang, et al.,The LRP5 high-bone-mass G171V mutation disrupts LRP5 interaction with Mesd, Mol Cell Biol. 24(11) ,2004 ,4677-4684.
International Search Report and Written Opinion for PCT International Application No. PCT/US2016/057814 dated Mar. 31, 2017.

* cited by examiner

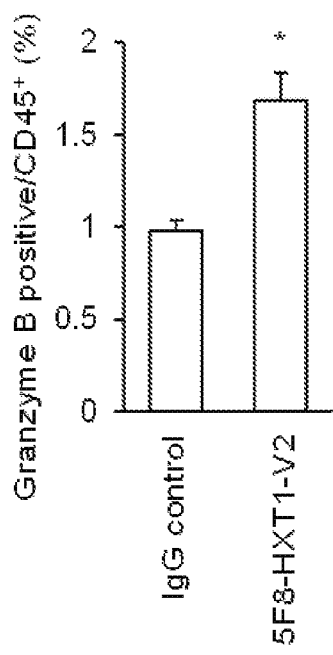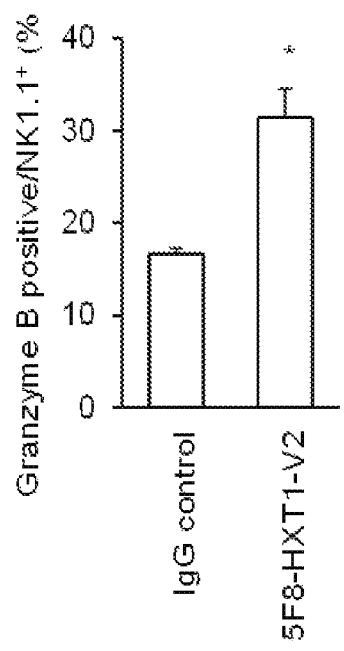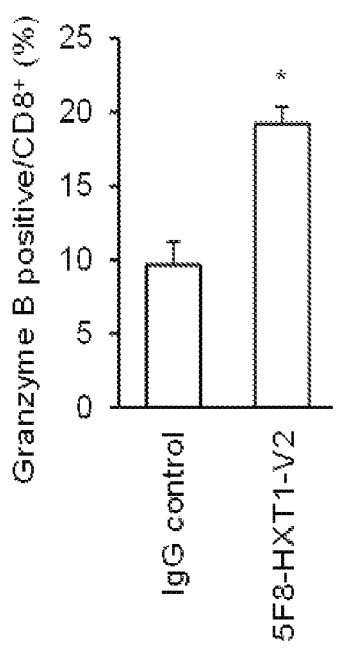
FIG. 13

Amino acid sequences of humanized anti-DKK2 antibodies.

Antibody humanization was based on mouse anti-DKK2 Y008-1-5F8 monoclonal antibody:

*(FIG. 16A) 5F8-HXT1-V1*
HC1 (IgG1), SEQ ID NO: 1
QVQVVQSGAEVKKPGASVKVSCKASGYSFTNYWMNWVRQAPGQGLEWMGMIHP
SDSETRLNQKFQGRVTLTVDKSSSTAYMELSSLRSEDTAVYYCAREGRLGLRSYA
MDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSL
SPGK

LC1 (Kappa), SEQ ID NO: 2
DIVMTQSPDSLAVSLGERATINCKSSQSLLNSSNQKNYLAWYQQKPGQPPKLLVYFA
STRESGVPDRFSGSGSGTDFTLTISSLQAEDVAVYFCQQHYITPLTFGGGTKVEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

*(FIG. 16B) 5F8-HXT1-V2*
HC2 (IgG1), SEQ ID NO: 3
QVQLVQSGSELKKPGASVKVSCKASGYIFTNYWMNWVRQAPGQGLEWMGMIHP
SDSETRLNQKFKDRVTITVDKSTSTAYMELSSLRSEDTAVYYCAREGRLGLRSYAM
DYWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK

LC1 (Kappa), SEQ ID NO: 2
DIVMTQSPDSLAVSLGERATINCKSSQSLLNSSNQKNYLAWYQQKPGQPPKLLVYFA
STRESGVPDRFSGSGSGTDFTLTISSLQAEDVAVYFCQQHYITPLTFGGGTKVEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC Note: Residues in bold and underlined denote those different between 5F8-HXT1-V1 and 5F8-HXT1-V2 of 5F8-HXT1. Residues in bold and highlighted in grey refer to complementarity determining regions (CDRs).

FIGS. 16A-16B

Amino acid sequence of Human DKK2, SEQ ID NO: 4

MAALMRSKDSSCCLLLLAAVLMVESSQIGSSRAKLNSIKSSLGGETPGQAANRSAGM
YQGLAFGGSKKGKNLGQAYPCSSDKECEVGRYCHSPHQGSSACMVCRRKKKRCHR
DGMCCPSTRCNNGICIPVTESILTPHIPALDGTRHRDRNHGHYSNHDLGWQNLGRPH
TKMSHIKGHEGDPCLRSSDCIEGFCCARHFWTKICKPVLHQGEVCTKQRKKGSHGLE
IFQRCDCAKGLSCKVWKDATYSSKARLHVCQKI

Amino acid sequence of Humanized 5F8 epitope derived from the above Human DKK2 sequence, SEQ ID NO: 5

KLNSIKSSLGGETPG

FIG. 18

```
SEQUENCE LISTING

<160> NUMBER OF SEQ ID NOS: 5

<210> SEQ ID NO 1
<211> LENGTH: 452
<212> TYPE: PRT
<213> ORGANISM: Artificial Sequence
<220> FEATURE:
<223> OTHER INFORMATION: Artificially synthesized humanized antibody

<400> SEQUENCE: 1

Gln Val Gln Val Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Thr Arg Leu Asn Gln Lys Phe
    50                  55                  60

Gln Gly Arg Val Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Glu Gly Arg Leu Gly Leu Arg Ser Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 2
<211> LENGTH: 220
<212> TYPE: PRT
<213> ORGANISM: Artificial Sequence
<220> FEATURE:
<223> OTHER INFORMATION: Artificially synthesized humanized antibody

<400> SEQUENCE: 2

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Pro Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ile Thr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 3
<211> LENGTH: 452
<212> TYPE: PRT
<213> ORGANISM: Artificial Sequence
<220> FEATURE:
<223> OTHER INFORMATION: Artificially synthesized humanized antibody

<400> SEQUENCE: 3

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Thr Arg Leu Asn Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Arg Leu Gly Leu Arg Ser Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140
```

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 4
<211> LENGTH: 259
<212> TYPE: PRT
<213> ORGANISM: Homo sapiens

<400> SEQUENCE: 4

Met Ala Ala Leu Met Arg Ser Lys Asp Ser Ser Cys Cys Leu Leu Leu
1               5                   10                  15

Leu Ala Ala Val Leu Met Val Glu Ser Ser Gln Ile Gly Ser Ser Arg
            20                  25                  30

Ala Lys Leu Asn Ser Ile Lys Ser Ser Leu Gly Gly Glu Thr Pro Gly
        35                  40                  45

Gln Ala Ala Asn Arg Ser Ala Gly Met Tyr Gln Gly Leu Ala Phe Gly
    50                  55                  60
```

```
Gly Ser Lys Lys Gly Lys Asn Leu Gly Gln Ala Tyr Pro Cys Ser Ser
65                  70                  75                  80

Asp Lys Glu Cys Glu Val Gly Arg Tyr Cys His Ser Pro His Gln Gly
                85                  90                  95

Ser Ser Ala Cys Met Val Cys Arg Arg Lys Lys Lys Arg Cys His Arg
            100                 105                 110

Asp Gly Met Cys Cys Pro Ser Thr Arg Cys Asn Asn Gly Ile Cys Ile
        115                 120                 125

Pro Val Thr Glu Ser Ile Leu Thr Pro His Ile Pro Ala Leu Asp Gly
    130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
            180                 185                 190

Phe Cys Cys Ala Arg His Phe Trp Thr Lys Ile Cys Lys Pro Val Leu
        195                 200                 205

His Gln Gly Glu Val Cys Thr Lys Gln Arg Lys Lys Gly Ser His Gly
    210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
            245                 250                 255

Gln Lys Ile

<210> SEQ ID NO 5
<211> LENGTH: 15
<212> TYPE: PRT
<213> ORGANISM: Artificial Sequence
<220> FEATURE:
<223> OTHER INFORMATION: Artificially synthesized humanized antibody
      epitope

<400> SEQUENCE: 5

Lys Leu Asn Ser Ile Lys Ser Ser Leu Gly Gly Glu Thr Pro Gly
1               5                   10                  15
```

HUMANIZED ANTI-DKK2 ANTIBODY AND USES THEREOF

CROSS-REFERENCE TO RELATED APPLICATIONS

This present application is a 35 U.S.C. § 371 national phase application from, and claims priority to, International Application No. PCT/US2016/057814, filed Oct. 20, 2016, and published under PCT Article 21(2) in English, which claims priority under 35 U.S.C. § 119(e) to U.S. Provisional Application No. 62/247,410, filed Oct. 28, 2015, all of which are incorporated herein by reference in their entireties.

STATEMENT REGARDING FEDERALLY SPONSORED RESEARCH OR DEVELOPMENT

This invention was made with government support under grant GM112182 awarded by National Institute of Health. The government has certain rights in the invention.

BACKGROUND OF THE INVENTION

Cancer is a major health problem worldwide. Each year, tens of millions of people are diagnosed with cancer around the world, and more than half of the patients eventually die from it. About one-half of all men and one-third of all women in the US will be diagnosed with a cancer at some point during their lifetime, and one in four deaths is caused by cancer (Jemal et al., CA Cancer J. Clin., 2002, 52:23-47; Howlader et al., SEER Cancer Statistics Review, 1975-2010, National Cancer Institute). The most-commonly identified human cancers include those that arise from organs and solid tissues, e.g., colon cancer, lung cancer, breast cancer, stomach cancer, prostate cancer, and endometrial cancer. Colon cancer affects 1 in 20 people in the western hemispheres (Henderson, Nature Cell Biology, 2000, 2(9): p. 653-60). Globally, every year 1 million new patients are diagnosed with colon cancer and half of them succumb to this disease (Liu et al., Cell, 2002, 108(6): p. 837-47).

In the past decades remarkable advancements in cancer treatment and diagnosis have occurred. Treatment options for cancer includes surgery, chemotherapy, radiation therapy, and immunotherapy. Most recently immunotherapy treatment, aiming on stimulating the immune system, has particularly attracted lots of investigations. Although immunotherapy could be highly efficacious, only subsets of patients regardless of the organ of origin of the tumor are usually responsive to therapy. New findings in this field are clearly needed for improving immunotherapy efficacy and specificity.

Wnt-signaling controls a wide variety of cell processes, including cell fate determination, differentiation, polarity, proliferation and migration. The Wnt family of secreted proteins bind to several classes of receptors, such as the low-density lipoprotein receptor related (LRP) proteins 5 and −6 (LRP5/6), resulting in activation of several different intracellular signaling cascades, including the Wnt/β-catenin, Wnt/calcium and Wnt/Jnk pathways. Binding of Wnts to LRP5/6 specifically activates the Wnt/β-catenin pathway by blocking the function of a multiprotein complex that primes β-catenin for degradation, resulting in accumulation of β-catenin in the cytoplasm and nucleus. Nuclear β-catenin complexes with members of the Lef/TCF family of transcription factors and activates gene expression.

Pathological states that may arise from altered stem cell function, such as degenerative diseases and cancer, are frequently associated with changes in Wnt/β-catenin pathway activity. Indeed, hyperactivation of the Wnt/β-catenin pathway is thought to induce premature senescence of stem cells and age-related loss of stem cell function (Brack et al., Science, 2007, Vol. 317 no. 5839 pp. 807-810; Liu et al., Science, 2007, Vol. 317 no. 5839 pp. 803-806). In cancer, hyperactivation of the Wnt/β-catenin pathway, often in conjunction with mutations in other cell growth regulatory genes, can lead to aberrant cell growth (Reya and Clevers, Nature, 2005, 434(7035):843-50). Thus, many ongoing investigations are focusing on Wnt/β-catenin pathway as a potential therapeutic target in cancer (Breuhahn et al., Oncogene, 2006, 25: 3787-3800; Greten et al., Br J Cancer, 2009, 100: 19-23). Particularly, several research studies including cancer genomic sequencing projects revealed that more than 80% of colon cancers harbor a mutation or even a loss of the adenomatosis polyposis coli (APC) gene, a major suppressor of the Wnt/β-catenin pathway (Kinzler and Vogelstein, Cell. 1996, Oct. 18; 87(2):159-70. Review; Sjoblom et al., Science, 2006, Oct. 13; 314(5797):268-74; Mann et al., Proc Natl Acad Sci USA, 1999. 96(4): p. 1603-8). APC and proteins such as GSK3β and Axin form a complex which marks β-catenin for degradation. Mutations in APC disrupt this complex and leads to increased levels of cytoplasmic β-catenin and its nuclear translocation. Since β-catenin is the most important adaptor of the Wnt signaling it promotes expression of oncogenic factors in response to Wnt ligands.

Wnt signaling is also regulated by a number of secreted polypeptide antagonists. These include four secreted Dickkopf (Dkk) proteins (Monaghan et al., Mech Dev, 1999. 87: 45-56; Krupnik et al., Gene, 1999. 238: 301-13). Among these four Dkk proteins, DKK1, 2 and 4 have been demonstrated to be effective antagonists of canonical Wnt signaling (Mao et al., Nature, 2001. 411: 321-5; Semenov et al., Curr Biol, 2001. 11: 951-61; Bafico et al., Nat Cell Biol, 2001. 3: 683-6; Niehrs, Nature, 2006. 25: 7469-81) by directly binding to Wnt coreceptor LRP 5/6 with high affinities (Mao et al., Nature, 2001. 411: 321-5; Semenov et al., Curr Biol, 2001. 11: 951-61; Bafico et al., Nat Cell Biol, 2001. 3: 683-6). While DKK1 is reported to play a crucial role in head and heart formation in vertebrate development (Niida et al., Oncogene, 2004, Nov. 4; 23(52):8520-6), Dkk2 does not appear to play critical roles in vertebrate development. Mice lacking Dkk2 have lower blood glucose (Li et al., Proc Natl Acad Sci USA, 2012. 109: 11402-7), reduced bone mass (Li et al., Nat Genet, 2005. 37: 945-52) and defective ocular surface epithelia (Gage et al., Dev Biol, 2008. 317: 310-24; Mukhopadhyay et al., Development, 2006. 133: 2149-54). Given that DKK proteins are Wnt antagonists, the conventional wisdom is that inactivation of DKK would increase Wnt activity and hence accelerate cancer formation. However, their roles in cancer formation has not been directly investigated.

The Dkk molecules contain two conserved cysteine-rich domains (Niehrs, Nature, 2006. 25: 7469-81). Previously, it was shown that the second Cys-rich domains of DKK1 and DKK2 played a more important role in the inhibition of canonical Wnt signaling (Li et al., J Biol Chem, 2002. 277: 5977-81; Brott and Sokol Mol. Cell. Biol., 2002. 22: 6100-10). More recently, the structure of the second Cys-rich domain of DKK2 was solved and delineated amino acid residues on the domain that are required for DKK interaction with LRP5/6 and those for Kremens (Chen et al., J Biol Chem, 2008. 283: 23364-70; Wang et al., J Biol Chem, 2008. 283: 23371-5). Dkk interaction with LRP5/6 underlie the primary mechanism for Dkk-mediated inhibition of Wnt. Although Dkk interaction with Kremen, also a transmembrane protein, was shown to facilitate Dkk antagonism of Wnt signaling, this interaction may have other unresolved functions. Ala scan mutagenesis identified amino acid residues on the third YWTD repeat domain of LRP5 as being important for binding to DKK1 and DKK2 (Zhang et al., Mol. Cell. Biol., 2004. 24: 4677-84). These results have been confirmed by the structural studies of a DKK1/LRP6 third and fourth YWTD repeat domain complex (Cheng et al., Nat Struct Mol Biol, 2011. 18: 1204-10; Chen et al., Dev Cell, 2011. 21: 848-61; Ahn et al., Dev Cell, 2011. 21: 862-73. Bourhis et al., Structure, 2011. 19: 1433-42). One of the structural studies also revealed a second DKK-LRP interaction site between the N-terminus of DKK and the first YWTD repeat domain of LRP (Bourhis et al., Structure, 2011. 19: 1433-42).

Although Wnt signaling was initially discovered for its role in early embryonic development and for its promotion of tumorigenesis, recent studies have revealed that is plays important roles in a wide range of biological processes. The present invention derives from unexpected discovery of a role of a Wnt antagonist, against the conventional wisdom, in tumor promotion. The neutralization of this Wnt inhibitor, which would result in alteration of Wnt signaling, inhibits tumor formation probably by modulating the tumor immune microenvironment.

Clearly there is a need of new ways to diminish cancer cell proliferation, to trigger cancer cell death, and to treat cancer. The current invention fulfills this need. Furthermore, the present invention satisfies the need for improving anti-cancer immunotherapy and cancer diagnosis.

SUMMARY OF THE INVENTION

The present invention relates to compositions and methods of treating a cancer in a subject in need thereof.

In one aspect, the method of treating a cancer comprises administering to the subject an effective amount of a humanized anti-Dickkopf2 (anti-DKK2) antibody or fragment thereof in a pharmaceutical acceptable carrier.

In another aspect, the invention includes a pharmaceutical composition for treating a cancer in a subject. The pharmaceutical composition of the invention comprises a humanized anti-Dickkopf2 (anti-DKK2) antibody or fragment thereof and a pharmaceutical acceptable carrier.

In another aspect, the invention includes a method for providing anti-tumor immunity in a subject. In yet another aspect, the invention includes a method for stimulating a T cell-mediated immune response to a cell population or tissue in a subject. The method of the invention comprises administering to the subject an effective amount of a humanized anti-Dickkopf2 (anti-DKK2) antibody or fragment thereof with a pharmaceutical acceptable carrier. In some embodiments, the T cell-mediated immune response is a $CD8^+$ cytotoxic T lymphocyte (CTL) response.

The invention also provides a method of diagnosing a cancer and a method of diagnosing a predisposition for developing a cancer in a subject. These methods comprise determining the expression level of a DKK2 gene in a biological sample from the subject, wherein an increase in the expression level of DKK2 in the biological sample from the subject as compared with the level of DKK2 expression in a control biological sample from a subject not having a cancer is an indication that the subject has a cancer or a predisposition for developing a cancer, and wherein when a cancer or a predisposition for developing a cancer is detected in a subject, a humanized anti-DKK2 antibody treatment is recommended for the subject.

The invention further provides a method for determining the efficacy of a humanized anti-DKK2 antibody treatment for cancer in a subject in need thereof. The method comprises determining the expression level of Dickkopf2 (DKK2) gene in a biological sample from the subject, wherein an increase in the expression level of DKK2 in the biological sample from the subject as compared with the level of DKK2 expression in a control biological sample from a subject not having a cancer is an indication that the humanized anti-DKK2 antibody treatment is effective, and wherein when the humanized anti-DKK2 antibody treatment is determined to be effective, an additional treatment is recommended for the subject.

In a further aspect, the invention includes a composition comprising a humanized anti-Dickkopf2 (anti-DKK2) antibody targeting a DKK2 epitope comprising the amino acid sequence SEQ ID NO: 5.

In yet a further aspect, the invention includes a kit for diagnosing a cancer or a predisposition for developing a cancer or a metastasis in a subject. The kit of the invention comprises a humanized anti-DKK2 antibody targeting a DKK2 epitope comprising the amino acid sequence SEQ ID NO: 5.

In some embodiments, the cancer comprises a tumor comprising cells that express an adenomatosis polyposis coli (APC) mutation. In some embodiments, the humanized anti-DKK2 antibody possesses neutralizing activity. In other embodiments, the humanized anti-DKK2 antibody targets a DDK2 neutralizing epitope comprising the amino acid sequence SEQ ID NO: 5. In yet other embodiments, the humanized anti-DKK2 antibody comprises at least one of the amino acid sequences selected from the group consisting of SEQ ID NOs: 1, 2 and 3.

In some embodiments, the cancer is selected from the group consisting of colorectal cancer, pancreatic cancer, gastric cancer, intestinal cancer, pancreatic cancer, and esophageal cancer. In some embodiments, the cancer is metastatic.

In some embodiments, the compositions and methods of the invention further comprise administering to the subject an additional agent selected from the group consisting of a chemotherapeutic agent, an anti-cell proliferation agent, an immunotherapeutic agent and any combination thereof. In some embodiments, the additional agent is a programmed cell death 1 (PD-1) antibody. In other embodiments, the humanized anti-DKK2 antibody and the additional agent are co-administered to the subject. In yet other embodiments, the humanized anti-DKK2 antibody and the additional agent are co-formulated and are co-administered to the subject.

In some embodiments, the route of administration is selected from the group consisting of inhalation, oral, rectal, vaginal, parenteral, topical, transdermal, pulmonary, intranasal, buccal, ophthalmic, intrathecal, and any combination thereof.

In some embodiments, the expression level of DKK2 in the biological sample from the subject is at least 10% greater than the normal control level. In some embodiments, the expression level of DKK2 in the biological sample from the subject or normal control is determined using a method selected from the group consisting of detecting mRNA of the gene, detecting a protein encoded by the gene, and detecting a biological activity of the protein encoded by the gene. In some embodiments, the additional treatment comprises at least one selected from the group consisting of chemotherapy, radiation therapy, immunotherapy and cancer vaccine therapy.

In some embodiments, the subject is a mammal. In other embodiments, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 13 is a series of histograms depicting the effect of humanized anti-DKK2 antibody 5F8-HXT1-V2 on NK and CD8 cell activation. 5F5-HXT1-V2 treatment increased Granzyme B-positive immune cells, including CD8 positive lymphocytes and NK1.1 positive neutral killer cells. *, p<0.05 vs. control IgG (n=5, Student's t-Test).

FIGS. 16A-16B are lists of the amino acid sequences of humanized anti-DKK2 antibodies. The antibody humanization was based on mouse anti-DKK2 5F8 monoclonal antibody (5F8 mAb). FIG. 16A: list of the amino acid sequences of one version of the humanized anti-DKK2 antibody, 5F8-HXT1-V1, comprising the heavy chain 1 (HC1, IgG1; SEQ ID NO: 1) and light chain 1 (LC1, Kappa; SEQ ID NO: 2). FIG. 16B: list of the amino acid sequences of a second version of the humanized anti-DKK2 antibody, 5F8-HXT1-V2, comprising the heavy chain 2 (HC2, IgG1; SEQ ID NO: 3) and light chain 1 (LC1, Kappa; SEQ ID NO: 2). The residues highlighted in red denote those different between 5F8-HXT1-V1 and 5F8-HXT1-V2. The residues in bold refer to complementarity determining regions (CDRs).

FIG. 18 is a list of the amino acid sequences of the antigen (SEQ ID NO: 4) and the derived epitope for humanized anti-DKK2 antibodies (SEQ ID NO: 5).

DETAILED DESCRIPTION OF THE INVENTION

Figure 1A:
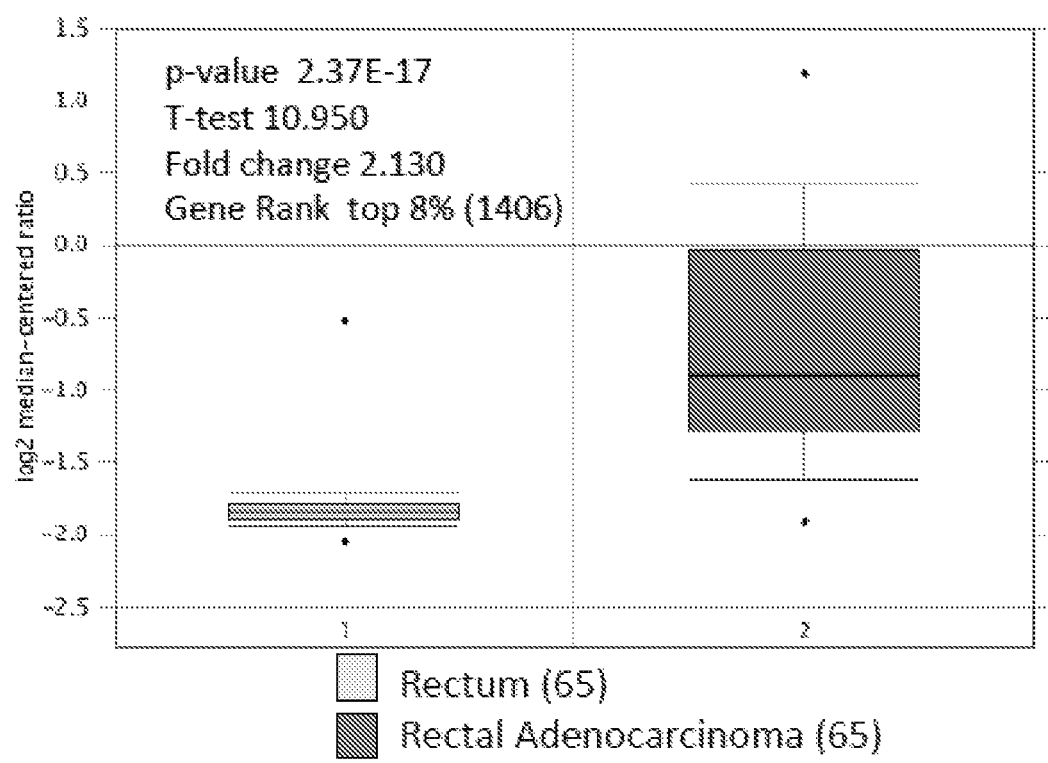
FIGS. 1A-1D are a series of box plots depicting the upregulation of DKK2 gene expression in human GI tumors based on the analysis of microarray data in the public domain.
Figure 1B:
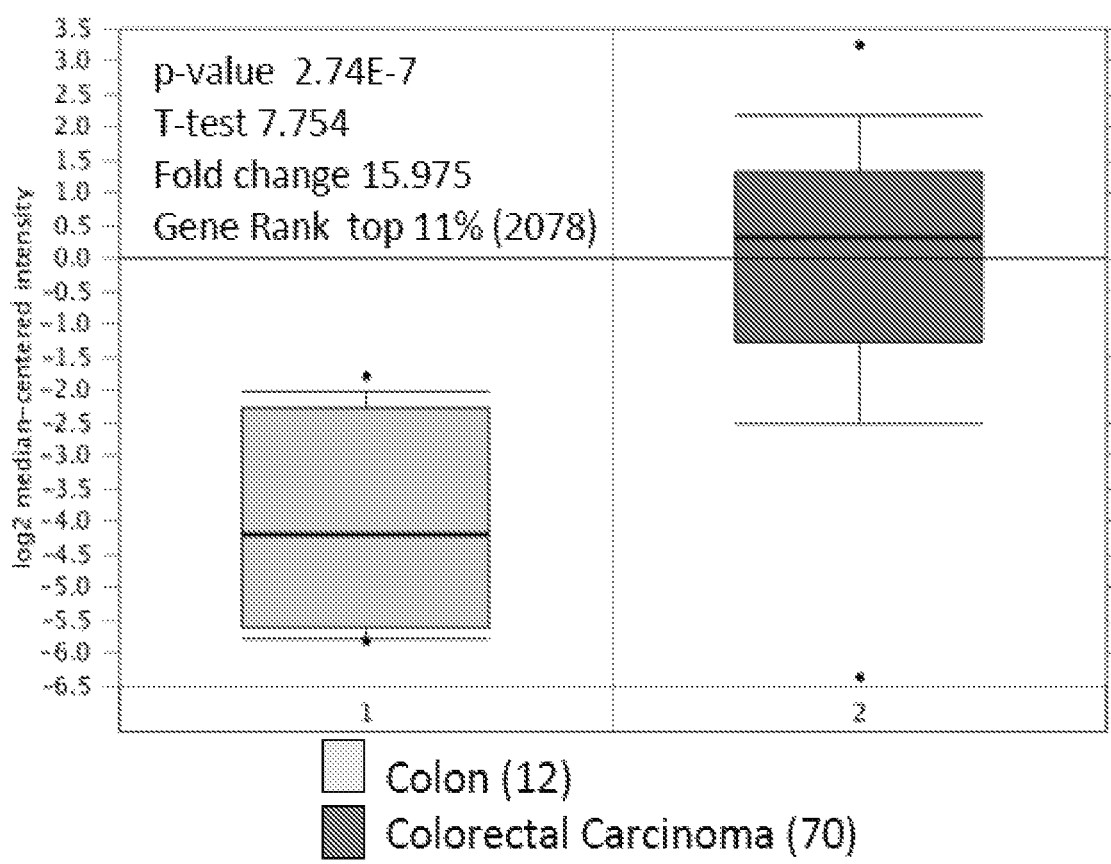
Figure 1C:
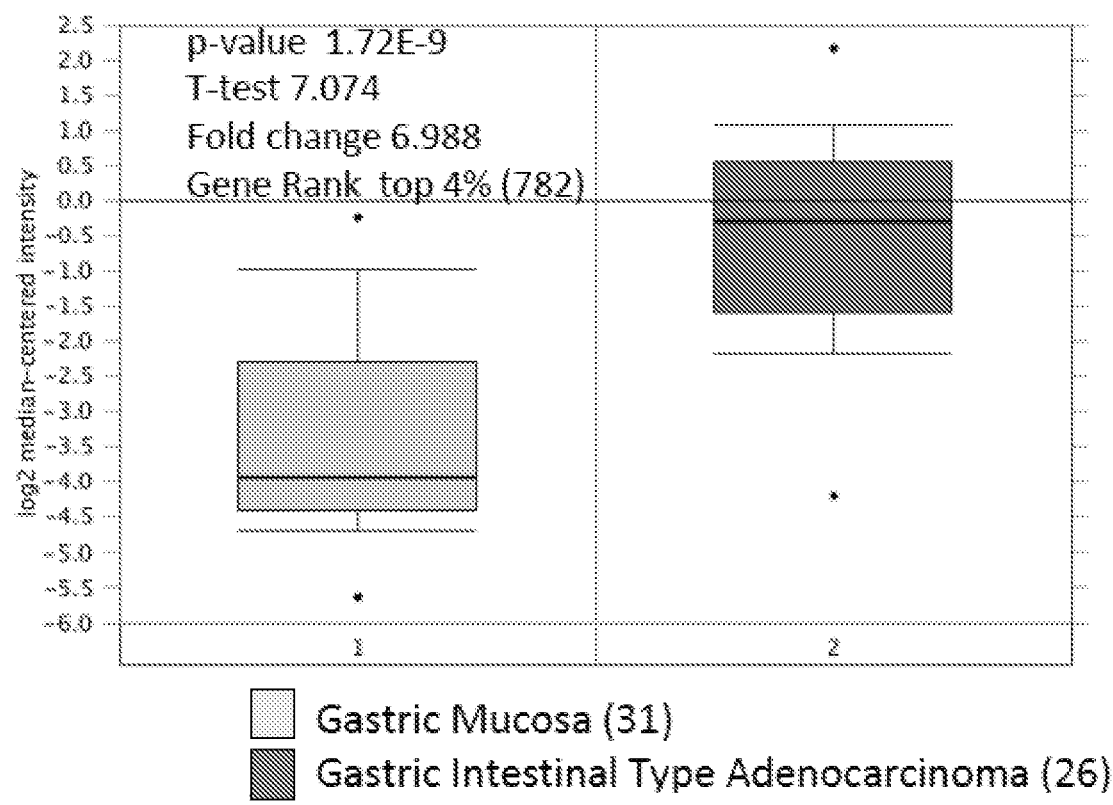
Figure 1D:
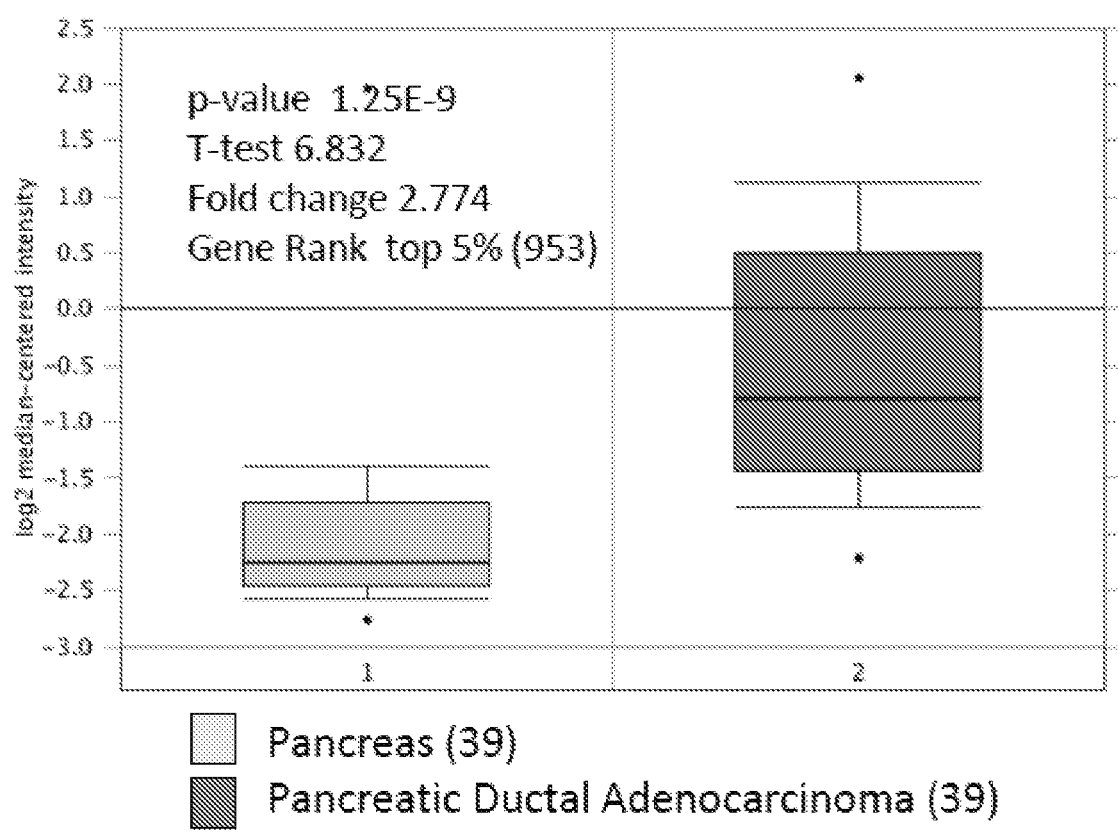

The present invention relates to the unexpected discovery that inhibition of Dickkopf2 (DKK2) results in suppression of tumors' formation accompanied by increased cytotoxic activity of immune effector cells including neutral killer (NK) cells and $CD8^+$ cytotoxic T lymphocytes (CTLs), and increased tumor cell apoptosis. Thus, in various embodiments described herein, the methods of the invention relate to methods of treating cancer by administering to a patient an effective amount of humanized anti-DKK2 antibody, methods for providing anti-tumor immunity in a subject, methods of stimulating immune effector cell-mediated immune responses to a cell population or a tissue in a subject. Additionally, the current invention includes methods of diagnosing a cancer or a predisposition of developing a cancer and methods for determining the use of immunotherapy treatment for treating cancer. Furthermore, the invention encompasses a pharmaceutical composition for treating cancer as well as a kit for carrying out the aforementioned methods.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of +20% or +10%, more preferably +5%, even more preferably +1%, and still more preferably +0.1% from the specified value, as such variations are appropriate to perform the disclosed methods.

As used herein, "10% greater" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control.

As used herein, the terms "control," or "reference" are used interchangeably, and refer to a value that is used as a standard of comparison (e.g., DKK2 level of expression in a healthy subject).

A "subject" or "patient," as used therein, may be a human or non-human mammal. Non-human mammals include, for example, livestock and pets, such as ovine, bovine, porcine, canine, feline and murine mammals. Preferably, the subject is human.

A "mutation" as used therein is a change in a DNA sequence resulting in an alteration from its natural state. The mutation can comprise deletion and/or insertion and/or duplication and/or substitution of at least one desoxyribonucleic acid base such as a purine (adenine and/or thymine) and/or a pyrimidine (guanine and/or cytosine) Mutations may or may not produce discernible changes in the observable characteristics (phenotype) of an organism (subject).

The term "immunogenicity" as used herein, is the ability of a particular substance, such as an antigen or epitope, to provoke an immune response in the body of a mammal. This immune response could be humoral and/or cell-mediated.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions.

Within the context of other cells, this term infers either up or down regulation of a particular physico-chemical process The term "activated T cells" indicates T cells that are currently undergoing cell division, cytokine production, performance of regulatory or cytolytic effector functions, and/or has recently undergone the process of "activation."

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

The term the "immunotherapeutic agent" as used herein is meant to include any agent that modulates the patient's immune system. "immunotherapy" refers to the treatment that alters the patient's immune system.

The term "therapeutic" as used herein means a treatment and/or prophylaxis. A therapeutic effect is obtained by suppression, remission, or eradication of a disease state.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes prevention of cancer.

The term "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

"DKK protein" refers to a protein of the Dkk family of proteins that contains one or more cysteine-rich domains. The Dkk family of proteins includes Dkk1, Dkk2, Dkk3 and Dkk4, and any other protein sufficiently related to one or more of these proteins at the sequence level, structurally or functionally. This family of proteins is described, e.g., in Krupnik et al. (1999) Gene 238:301. Allelic variants and mutants of Dkk proteins such as those recited herein are also encompassed by this definition.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Hybridization" refers to any process by which a strand of nucleic acid binds with a complementary strand through base pairing. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. Hybridization also includes the formation of duplexes which contain certain mismatches, provided that the two strands are still forming a double stranded helix. "Stringent hybridization conditions" refers to hybridization conditions resulting in essentially specific hybridization. The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. An "isolated cell" or "isolated population of cells" is a cell or population of cells that is not present in its natural environment.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

A "stem cell" refers to a cell that is capable of differentiating into a desired cell type. A stem cell includes embryonic stem (ES) cells; adult stem cells; and somatic stem cells, such as SP cells from uncommitted mesoderm. A "totipotent" stem cell is capable of differentiating into all tissue types, including cells of the meso-, endo-, and ectoderm. A "multipotent" or "pluripotent" stem cell is a cell which is capable of differentiating into at least two of several fates.

The term "variant," when used in the context of a polynucleotide sequence, may encompass a polynucleotide sequence related to that of a gene or the coding sequence thereof. This definition may also include, for example, "allelic," "splice," "species," or "polymorphic" variants. The polypeptides generally will have significant amino acid identity relative to each other. A polymorphic variant is a variation in the polynucleotide sequence of a particular gene between individuals of a given species. Polymorphic variants may encompass "single nucleotide polymorphisms" (SNPs) in which the polynucleotide sequence varies by one base. The presence of SNPs may be indicative of, for example, a certain population, a disease state, or a propensity for a disease state.

The term "Wnt antagonist" or "Wnt inhibitor" refers to a molecule or composition which downregulates (e.g., suppresses or inhibits) signal transduction via the Wnt pathway. Downregulation may occur directly, e.g., by inhibiting a bioactivity of a protein in a Wnt signaling pathway, or indirectly, e.g., by inhibiting downstream mediators of Wnt signaling (such as TCF3) or by decreasing stability of β-catenin, etc. Examples of Wnt antagonists include, but are not limited to, Dkk polypeptides (Glinka et al., Nature, 1998, 391: 357-62; Niehrs, Trends Genet, 1999, 15(8):314-9), crescent polypeptides (Marvin et al., Genes & Dev., 2001, 15: 316-327), cerberus polypeptides (U.S. Pat. No. 6,133, 232), WISE/Sclerostin (Li et al., J Biol Chem, 2005. 280:

19883-7), axin polypeptides (Zeng et al., Cell, 1997, 90(1): 181-92; Itoh et al., Curr Biol, 1998, 8(10):591-4; Willert et al., Development, 1999, 126(18):4165-73), Frzb polypeptides (Cadigan et al., Cell, 1998, 93(5):767-77; U.S. Pat. Nos. 6,133,232; 6,485,972; glycogen synthase kinase (GSK) polypeptides (He et al., Nature, 1995) 374(6523): 617-22), T-cell factor (TCF) polypeptides (Molenaar et al., Cell, 1996, 86(3):391-9), dominant negative dishevelled polypeptides (Wallingford et al., Nature, 2000, 405(6782): 81-5), dominant negative N-cadherin polypeptides (U.S. Pat. No. 6,485,972), dominant negative β-catenin polypeptides (U.S. Pat. No. 6,485,972), dominant negatives of downstream transcription factors (e.g., TCF, etc.), dominant negatives of Wnt polypeptides, agents that disrupt LRP-frizzled-wnt complexes, and agents that sequester Wnts (e.g., crescent and antibodies to Wnts). Wnt antagonist polypeptides may be of mammalian origin, e.g., human, mouse, rat, canine, feline, bovine, or ovine, or non-mammalian origin, e.g., from *Xenopus*, zebrafish, *Drosophila*, chicken, or quail. Wnt antagonists also encompass fragments, homologs, derivatives, allelic variants, and peptidomimetics of various polypeptides, including, but not limited to, Dkk, crescent, cerberus, axin, Frzb, GSK, TCF, dominant negative dishevelled, dominant negative N-cadherin, and dominant negative β-catenin polypeptides. In other embodiments, Wnt antagonists also include antibodies (e.g., Wnt-specific antibodies), polynucleotides and small molecules.

The term "cancer" as used herein, includes any malignant tumor including, but not limited to, carcinoma, sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof.

The term "carcinoma" refers to a malignant new growth made up of epithelial cells tending to infiltrate surrounding tissues, and to give rise to metastases.

The term "cancer vaccine" refers to a vaccine that stimulates the immune system to fight a cancer or to fight the agents that contribute to the development of a cancer. There are two broad types of cancer vaccines: Preventive cancer vaccines, which are intended to prevent cancer from developing in a healthy subject; and therapeutic cancer vaccines, which are intended to treat an existing cancer by strengthening the body's natural defenses against the cancer (Lollini et al., Nature Reviews Cancer, 2006; 6(3):204-216). As used herein the term "cancer vaccine" should be construed to include both preventive and therapeutic cancer vaccines.

The term "metastasis" refers to the spread of a cancer from one organ or part to another non-adjacent organ or part.

The term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "antibody" or "Ab" as used herein, refers to a protein, or polypeptide sequence derived from an immunoglobulin molecule which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

By the term "synthetic antibody" as used herein, is meant an antibody generated using recombinant DNA technology, such as, for example, an antibody expressed by a bacteriophage as described herein. The term should also be construed to mean an antibody generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotide aptamer is a DNA or RNA molecule, usually comprising several strands of nucleic acids, that adopts highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

The term "anti-tumor effect" as used herein, refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "xenograft" as used herein, refers to a graft of tissue taken from a donor of one species and grafted into a recipient of another species.

The term "allograft" as used herein, refers to a graft of tissue taken from a donor of one species and grafted into a recipient of the same species Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The immune system is balanced between activation and suppression. Evasion of immunosurveillance is one of the prerequisites for tumor formation. One of the ways for tumors to evade immunosurveillance is to produce elevated amount of immunosuppressive molecules. Increasing number of immunosuppressive molecules and mechanisms have been identified over the years. Neutralization of these immunosuppressive molecules has been shown to be efficacious in treating various malignancies.

The present invention relates to the discovery of a secreted tumor formation enhancer DKK2 that suppresses neutral killer (NK) cell and $CD8^+$ cytotoxic T lymphocyte (CTL) activity. DKK2 is a secreted protein, which can inhibit β-catenin-mediated Wnt signaling, alter non-β-catenin-mediated Wnt activity, and may also have Wnt-independent functions. DKK2 is expressed in many tissues and is upregulated in human colorectal, gastric intestinal, liver, kidney, and pancreatic cancers. Experimental evidence described below indicates that DKK2 inhibitors and neutralizing antibodies are key immunomodulators for treating cancers in which DKK2 is expressed. Thus DKK2 is a promising target for treating these cancers.

Methods of the Invention

The present invention is directed to a method of treating cancer in a subject in need thereof the method comprising administering to the subject an effective amount of a humanized anti-DKK2 antibody or fragment thereof in a pharmaceutical acceptable carrier. The humanized anti-DKK2 antibody of the invention inhibits or reduces expression of DKK2 and/or inhibits or reduces DKK2 activity in a cell, tissue or bodily fluid.

Antibodies

The invention includes a composition comprising a humanized anti-DKK2 antibody. In one embodiment, the humanized anti-DKK2 antibody comprises at least one of the amino acid sequences selected from the group consisting of SEQ ID NOs: 1, 2 and 3 (FIGS. 16A-16B).

Methods of producing antibodies are known in the art. Exemplary techniques for the production of the antibodies used in accordance with the present invention are herein described. It will be appreciated by one skilled in the art that an antibody comprises any immunoglobulin molecule, whether derived from natural sources or from recombinant sources, which is able to specifically bind to an epitope present on a target molecule. In one embodiment, the target molecule comprises When the antibody to the target molecule used in the compositions and methods of the invention is a polyclonal antibody (IgG), the antibody is generated by inoculating a suitable animal with a peptide comprising full length target protein, or a fragment thereof, an upstream regulator, or fragments thereof. These polypeptides, or fragments thereof, may be obtained by any methods known in the art, including chemical synthesis and biological synthesis.

Antibodies produced in the inoculated animal that specifically bind to the target molecule, or fragments thereof, are then isolated from fluid obtained from the animal. Antibodies may be generated in this manner in several non-human mammals such as, but not limited to goat, sheep, horse, camel, rabbit, and donkey. Methods for generating polyclonal antibodies are well known in the art and are described, for example in Harlow et al., 1998, In: Antibodies, A Laboratory Manual, Cold Spring Harbor, N.Y.

Monoclonal antibodies directed against a full length target molecule, or fragments thereof, may be prepared using any well-known monoclonal antibody preparation procedures, such as those described, for example, in Harlow et al. (1998, In: Antibodies, A Laboratory Manual, Cold Spring Harbor, N.Y.) and in Tuszynski et al. (1988, Blood, 72:109-115). Human monoclonal antibodies may be prepared by the method described in U.S. Patent Publication No. 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al., 1992, Critical Rev. Immunol. 12(3,4):125-168, and the references cited therein.

When the antibody used in the methods of the invention is a biologically active antibody fragment or a synthetic antibody corresponding to antibody to a full length target molecule, or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology available in the art, and described, for example, in Wright et al., 1992, Critical Rev. in Immunol. 12(3,4): 125-168 and the references cited therein. Alternatively, quantities of the desired antibody or fragment thereof may also be synthesized using chemical synthesis technology. If the amino acid sequence of the antibody is known, the desired antibody can be chemically synthesized using methods known in the art.

In one embodiment, the present invention includes the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule.

In some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol.

Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

In some embodiments, an expression control DNA sequence can be operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, 1979, which is incorporated herein by reference).

DNA sequences of human antibodies and particularly the complementarity determining regions (CDRs) can be isolated in accordance with procedures well known in the art. Preferably, the human CDRs DNA sequences are isolated from immortalized B-cells as described in International Patent Application Publication No. WO 1987/02671. CDRs useful in producing the antibodies of the present invention may be similarly derived from DNA encoding monoclonal antibodies capable of binding to the target molecule. Such humanized antibodies may be generated using well-known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

Another method of generating specific antibodies, or antibody fragments, reactive against a DKK2 involves the screening of expression libraries encoding immunoglobulin genes, or portions thereof, expressed in bacteria with a DKK2 protein or peptide. For example, complete Fab fragments, VH regions and Fv regions can be expressed in bacteria using phage expression libraries. See for example, Ward et al., Nature, 1989, 341: 544-546; Huse et al., Science, 1989, 246: 1275-1281; and McCafferty et al., Nature, 1990, 348: 552-554. Screening such libraries with, for example, a DKK2 peptide, can identify immunoglobulin fragments reactive with DKK2. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., Nature, 1990, 348: 552-554. Clackson et al., Nature, 1991, 352: 624-628 and Marks et al., J Mol Biol, 1991, 222: 581-597 describe the isolation of murine and human antibodies, respectively, using phage libraries. Subsequent publications describe the production of high affinity (nM range) human antibodies by chain shuffling (Marks et al., BioTechnology, 1992, 10: 779-783), as well as combinatorial infection and in vivo recombination as a strategy for constructing very large phage libraries (Waterhouse et al., Nuc. Acids. Res., 1993, 21: 2265-2266). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 1984, 81: 6851), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen combining site of an antibody to create a chimeric bivalent antibody having one antigen-combining site with specificity for a first antigen and another antigen-combining site with specificity for a different antigen.

Various techniques have been developed for the production of functional antibody fragments. The antibody fragment may include a variable region or antigen-binding region of the antibody. Traditionally, these fragments were derived via proteolytic digestion of intact antibodies (see, e.g., Morimoto et al., Journal of Biochemical and Biophysical Methods, 1992, 24: 107-117 and Brennan et al., Science, 1985, 229: 81). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F (ab') 2 fragments (Carter et al., Bio/Technology, 1992, 10: 163-167). According to another approach, F (ab') 2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

Antibody mimics or "non-antibody binding protein" use non-immunoglobulin protein scaffolds, including adnectins, avimers, single chain polypeptide binding molecules, and antibody-like binding peptidomimetics by using non-immunoglobulin protein scaffolds as alternative protein frameworks for the variable regions of antibodies (U.S. Pat. Nos. 5,260,203; 5,770,380; 6,818,418 and 7,115,396). Other compounds have been developed that target and bind to targets in a manner similar to antibodies. Certain of these "antibody mimics" use non-immunoglobulin protein scaffolds as alternative protein frameworks for the variable regions of antibodies. A methodology for reducing antibodies into smaller peptidomimetics, termed "antibody like binding peptidomimetics" (ABiP) can be used, a methodology for reducing antibodies into smaller peptidomimetics, can also be useful as an alternative to antibodies (Murali et al. Cell Mol Biol., 2003, 49(2):209-216).

Fusion proteins that are single-chain polypeptides including multiple domains termed "avimers" were developed from human extracellular receptor domains by in vitro exon shuffling and phage display and are a class of binding proteins somewhat similar to antibodies in their affinities and specificities for various target molecules (Silverman et al. Nat Biotechnol, 2005, 23: 1556-1561). The resulting multidomain proteins can include multiple independent binding domains that can exhibit improved affinity (in some cases sub-nanomolar) and specificity compared with single-epitope binding proteins. Additional details concerning methods of construction and use of avimers are disclosed, for example, in US Pat. App. Pub. Nos. 20040175756, 20050048512, 20050053973, 20050089932 and 20050221384.

In addition to non-immunoglobulin protein frameworks, antibody properties have also been mimicked in compounds including, but not limited to, RNA molecules and unnatural oligomers (e.g., protease inhibitors, benzodiazepines, purine derivatives and beta-turn mimics) all of which are suitable for use with the present invention. These are aimed to circumvent the limitations of developing antibodies in animals by developing wholly in vitro techniques for designing antibodies of tailored specificity.

As known in the art, aptamers are macromolecules composed of nucleic acid that bind tightly to a specific molecular target. Tuerk and Gold (Science, 1990, 249:505-510) discloses SELEX (Systematic Evolution of Ligands by Exponential Enrichment) method for selection of aptamers. In the SELEX method, a large library of nucleic acid molecules (e.g., 1015 different molecules) is produced and/or screened with the target molecule. Isolated aptamers can then be further refined to eliminate any nucleotides that do not contribute to target binding and/or aptamer structure (i.e., aptamers truncated to their core binding domain). See, e.g., Jayasena, 1999, Clin. Chem. 45:1628-1650 for review of aptamer technology.

The term "neutralizing" in reference to an anti-DKK2 antibody of the invention or the phrase "antibody that neutralizes DKK2 activity" is intended to refer to an antibody whose binding to or contact with DKK2 results in inhibition of a cell proliferative activity, metastasis of cancer, invasion of cancer cells or migration of cancer cells, inhibition of Wnt signaling, establishment of tumor-formation promoting microenvironment induced by DKK2. Because the DKK2 is secreted to extracellular and functions as an essential factor of proliferation, migration, invasion and metastasis of cancer cells, some anti-DKK2 antibodies may neutralize these activity. The neutralizing antibody in this invention is especially useful in therapeutic applications: to prevent or treat intractable diseases cancers, and cancer metastasis. The neutralizing antibody in this invention can be administered to a patient, or contacted with a cell for inhibiting metastasis of a cancer characterized by the over-expression of DKK2.

The antibody of the present invention can be assessed for immunospecific binding by any method known in the art. The immunoassays that can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Current Protocols in Molecular Biology, (Ausubel et al., eds.), Greene Publishing Associates and Wiley-Interscience, New York, 2002).

Combination Therapies

The compounds identified in the methods described herein may also be useful in the methods of the invention when combined with at least one additional compound useful for treating cancer. The additional compound may comprise a compound identified herein or a compound, e.g., a commercially available compounds, known to treat, prevent, or reduce the symptoms of cancer and/or metastasis.

In one aspect, the present invention contemplates that the agents useful within the invention may be used in combination with a therapeutic agent such as an anti-tumor agent, including but not limited to a chemotherapeutic agent, immunotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include aclacinomycin, actinomycin, anthramycin, azaserine, bleomycins, cactinomycin, calicheamicin, carubicin, caminomycin, carzinophilin, chromomycin, dactinomycin, daunorubicin, detorubicin, 6-diazo-5-oxo-L-norleucine, doxorubicin, epirubicin, esorubicin, idarubicin, marcellomycin, mitomycins, mitoxantrone, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine.

Other examples of chemotherapeutic agents include, but are not limited to, the following and their pharmaceutically acceptable salts, acids and derivatives: nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatrexate; defofamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK@ razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLO, Bristol-Myers Squibb Oncology, Princeton, N.J.) and docetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriamine-pentaacetic acid, irofulven, Diptheria Toxin, mitogillin, ricin, botulinum toxin, cholera toxin, saporin 6, or a combination thereof.

An immunotherapeutic agent may be, but is not limited to, an interleukin-2 or other cytokine, an inhibitor of programmed cell death protein 1 (PD-1) signaling such as a monoclonal antibody that binds to PD-1, Ipilimumab. The immunotherapeutic agent can also block cytotoxic T lymphocytes associated antigen A-4 (CTLA-4) signaling and it can also relate to cancer vaccines and dendritic cell-based therapies.

The immunotherapeutic agent can further be NK cells that are activated and expanded by means of cytokine treatment or by transferring exogenous cells by adoptive cell therapy and/or by hematopoietic stem cell transplantation. NK cells suitable for adoptive cell therapy can be derived from different sources, including ex vivo expansion of autologous NK cells, unstimulated or expanded allogeneic NK cells from peripheral blood, derived from CD34+ hematopoietic progenitors from peripheral blood and umbilical cord blood, and NK-cell lines. Genetically modified NK cells expressing chimeric antigen receptors or cytokines are also contemplated in this invention. Another immunotherapeutic agent useful for this invention is an agent based on adoptive T cell therapy (ACT) wherein tumor-infiltrating lymphocytes (TILs) are administered to patients. The administered T cells can be genetically engineered to express tumor-specific antigen receptors such as chimeric antigen receptors (CARs), which recognize cell-surface antigens in a non-major histocompatibility (MHC)-restricted manner; or they can be traditional αβ TCRs, which recognize epitopes of intracellular antigens presented by MHC molecules.
Pharmaceutical Compositions and Formulations.

The invention envisions the use of a pharmaceutical composition comprising a humanized anti-DKK2 antibody for use in the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions are formulated using one or more pharmaceutically acceptable excipients or carriers. In one embodiment, the pharmaceutical compositions comprise a therapeutically effective amount of humanized anti-DKK2 antibody and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Administration/Dosing

The regimen of administration may affect what constitutes an effective amount. For example, the therapeutic formulations may be administered to the patient either prior to or after a surgical intervention related to cancer, or shortly after the patient was diagnosed with cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

Routes of Administration

One skilled in the art will recognize that although more than one route can be used for administration, a particular route can provide a more immediate and more effective reaction than another route.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration. Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Immune Response Stimulation.

In one embodiment, the invention comprises methods for providing anti-tumor immunity and for stimulating T-cell mediated immune response by administering the to the subject an effective amount of a humanized anti-DKK2 antibody or fragment thereof with a pharmaceutical acceptable carrier.

The activation T lymphocytes (T cells) and its use within immunotherapy for the treatment of cancer and infectious diseases, is well known in the art (Melief et al., Immunol. Rev., 1995, 145:167-177; Riddell et al., Annu. Rev. Immunol., 1995, 13:545-586). As disclosed in the current invention, elimination of DKK2 leads to an activation of CD8+ cytotoxic T lymphocytes (CTL) and suppression of tumors.

Markers for CTL activation could be, but are not limited to, cytotoxins such as perforin, granzymes, and granulysin, cytokines, IL-2, IL-4, CD25, CD54, CD69, CD38, CD45RO, CD49d, CD40L, CD137, CD134. The measurement in a sample of level of at least one of these markers can be used to assess CTL activation as presented herein the Examples section. Sorting of T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

Diagnosis and Treatment

In one embodiment, the invention relates to a method of diagnosing a cancer or a predisposition for developing a cancer or a metastasis in a subject. The method comprises determining the expression level of DKK2 gene in a biological sample from the subject, wherein an increase in the expression level of DKK2 as compared with a normal control level of DKK2 expression is an indication that the subject has cancer or has a predisposition for developing a cancer or metastasis. A humanized anti-DKK2 antibody, as disclosed herein, is used in the method of the invention to determine the expression level of DKK2 in the biological sample.

In another embodiment, the invention relates to a method for determining the efficacy of immunotherapy treatment for treating cancer in a subject in need thereof. The method comprises determining the expression level of DKK2 gene in a biological sample from the subject, wherein an increase in the expression level of DKK2 as compared with the expression level of DKK2 in a normal control is an indication that immunotherapy treatment will effective. In some aspects of the invention, treatment of cancer may include the treatment of solid tumors or the treatment of metastasis. Metastasis is a form of cancer wherein the transformed or malignant cells are traveling and spreading the cancer from one site to another. Such cancers include cancers of the skin, breast, brain, cervix, testes, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, moles dysplastic nevi, lipoma, angioma, dermatofibroma, keloids, and psoriasis. A humanized anti-DKK2 antibody, as disclosed herein, is used in the method of the invention to determine the expression level of DKK2 in the biological sample.

Control Standard Amount of Expression of DKK2

The method of the invention includes comparing a measured amount of expression of DKK2 in a biological sample from a subject to a control amount (i.e. the reference) of expression of DKK2.

In one embodiment, the standard control level of expression of DKK2 may be obtained by measuring the expression level of DKK2 in a healthy subject. Preferably, the healthy subject is a subject of similar age, gender and race and has never been diagnosed with any type of sever disease particularly any type of cancer.

In another embodiment, the control amount of expression of DKK2 is a value for expression of DKK2 that is accepted in the art. This reference value can be baseline value calculated for a group of subjects based on the average or mean values of DKK2 expression by applying standard statistically methods In one embodiment, the expression level is determined by a method selected from the group consisting of detecting mRNA of the gene, detecting a protein encoded by the gene, and detecting a biological activity of the protein encoded by the gene.

In certain aspects of the present invention, the expression level of DKK2 is determined in a sample from a subject. The sample preferably includes tumor cells, any fluid from the surrounding of tumor cells (i.e., leukemic blood, tumor tissue, etc. . . . ) or any fluid that is in physiological contact or proximity with the tumor, or any other body fluid in addition to those recited herein should also be considered to be included in the invention. A humanized anti-DKK2 antibody, as disclosed herein, is used in the method of the invention to determine the expression level of DKK2 in the biological sample.

Methods of Measurement

Any method known to those in the art can be employed for determining the level of DKK2 expression. For example, a microarray can be used. Microarrays are known in the art and consist of a surface to which probes that correspond in sequence to gene products (e.g. mRNAs, polypeptides, fragments thereof etc.) can be specifically hybridized or bound to a known position. To detect at least one gene of interest, a hybridization sample is formed by contacting the test sample with at least one nucleic acid probe. The nucleic acid probe can be, for example, a full-length nucleic acid molecule, or a portion thereof, such as an oligonucleotide of at least 10, 15, or 20 nucleotides in length and sufficient to specifically hybridize under stringent conditions to the appropriate target. In the instance of the present invention, in some embodiments, the probe for detecting DKK2 is a labeled nucleic acid probe capable of hybridizing to a human DKK2 mRNA or a fragment thereof. In other embodiments, the sequence of the nucleic acid probe is a nucleic acid sequence encoding one or a fragment of the amino acid sequences selected from the group consisting of SEQ ID NOs: 1, 2 and 3 (FIGS. 16A-16B). The hybridization sample is maintained under conditions which are sufficient to allow specific hybridization of the nucleic acid probe to a target of interest. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and a gene in the test sample, the sequence that is present in the nucleic acid probe is also present in the mRNA of the subject. More than one nucleic acid probe can also be used. Hybridization intensity data detected by the scanner are automatically acquired and processed by the Affymetrix Microarray Suite (MASS) software. Raw data is normalized to expression levels using a target intensity of 150. An alternate method to measure mRNA expression profiles of a small number of different genes is by e.g. either classical TaqMan® Gene Expression Assays or TaqMan® Low Density Array-micro fluidic cards (Applied Biosystems). Particularly, this invention preferably utilizes a qPCR system. Non-limiting examples include commercial kits such as the PrimePCRPathways® commercially available from Bio-rad (Berkley, Calif.).

The transcriptional state of a sample, particularly mRNAs, may also be measured by other nucleic acid expression technologies known in the art. mRNA can be isolated from the sample using any method known to those in the art. Non-limiting examples include commercial kits, such as the RNeasy® commercially available from Qiagen (Netherlands) or the Mini Kit the TRI Reagent® commercially available from Molecular Research Center, Inc. (Cincinnati, Ohio), can be used to isolate RNA. Generally, the isolated mRNA may be amplified using methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, New York (1995).

Another accurate method for profiling mRNA expression can the use of Next Generation Sequencing (NGS) including first, second, third as well as subsequent Next Generations Sequencing technologies.

In other aspects of the present invention, determining the amount or detecting the biological activity of a peptide, polypeptide can be achieved by all known means in the art for determining the amount of a peptide or polypeptide in a sample. These means comprise immunoassay devices and methods which may utilize labeled molecules in various sandwich, competition, or other assay formats. Such assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Kit

The invention includes a set of preferred antibodies, either labeled (e.g., fluorescer, quencher, etc.) or unlabeled, that are useful for the detection of at least DKK2.

In certain embodiments, a kit is provided. Commercially available kits for use in these methods are, in view of this specification, known to those of skill in the art. In general, kits will comprise a detection reagent that is suitable for detecting the presence of a polypeptide or nucleic acid, or mRNA of interest.

In another embodiment, there is a panel of probe sets or antibodies. In some embodiments, the panel of antibodies comprises a humanized anti-DKK2 antibody targeting a DKK2 epitope comprising at least one of the amino acid sequences selected from the group consisting of SEQ ID NOs: 4 and 5 (FIG. 18). In some embodiments, the panel of probe sets is designed to detect the level of DKK2 and provide information about cancer diagnosis or the predisposition of developing a cancer or a metastasis. Probe sets are particularly useful because they are smaller and cheaper than probe sets that are intended to detect as many peptides as possible in a particular genome. In the present invention, the probe sets are targeted at the detection of polypeptides that are informative about cancer genes. Probe sets may also comprise a large or small number of probes that detect peptides that are not informative about cancer. Such probes are useful as controls and for normalization (e.g., spiked-in markers). Probe sets may be a dry mixture or a mixture in solution. In some embodiments, probe sets can be affixed to a solid substrate to form an array of probes. The probes may be antibodies, or nucleic acids (e.g., DNA, RNA, chemically modified forms of DNA and RNA), LNAs (Locked nucleic acids), or PNAs (Peptide nucleic acids), or any other polymeric compound capable of specifically interacting with the peptides or nucleic acid sequences of interest.

It is contemplated that kits may be designed for isolating and/or detecting peptides (e.g. DKK2, know cancer markers, immune activators or apoptotic proteins) or nucleic acid sequences in essentially any sample (e.g., leukemic blood, tumor cells, tumor tissue, etc.), and a wide variety of reagents and methods are, in view of this specification, known in the art.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: DKK2 is Expressed in a Wide Range of Solid Tumors

Figure 2A:
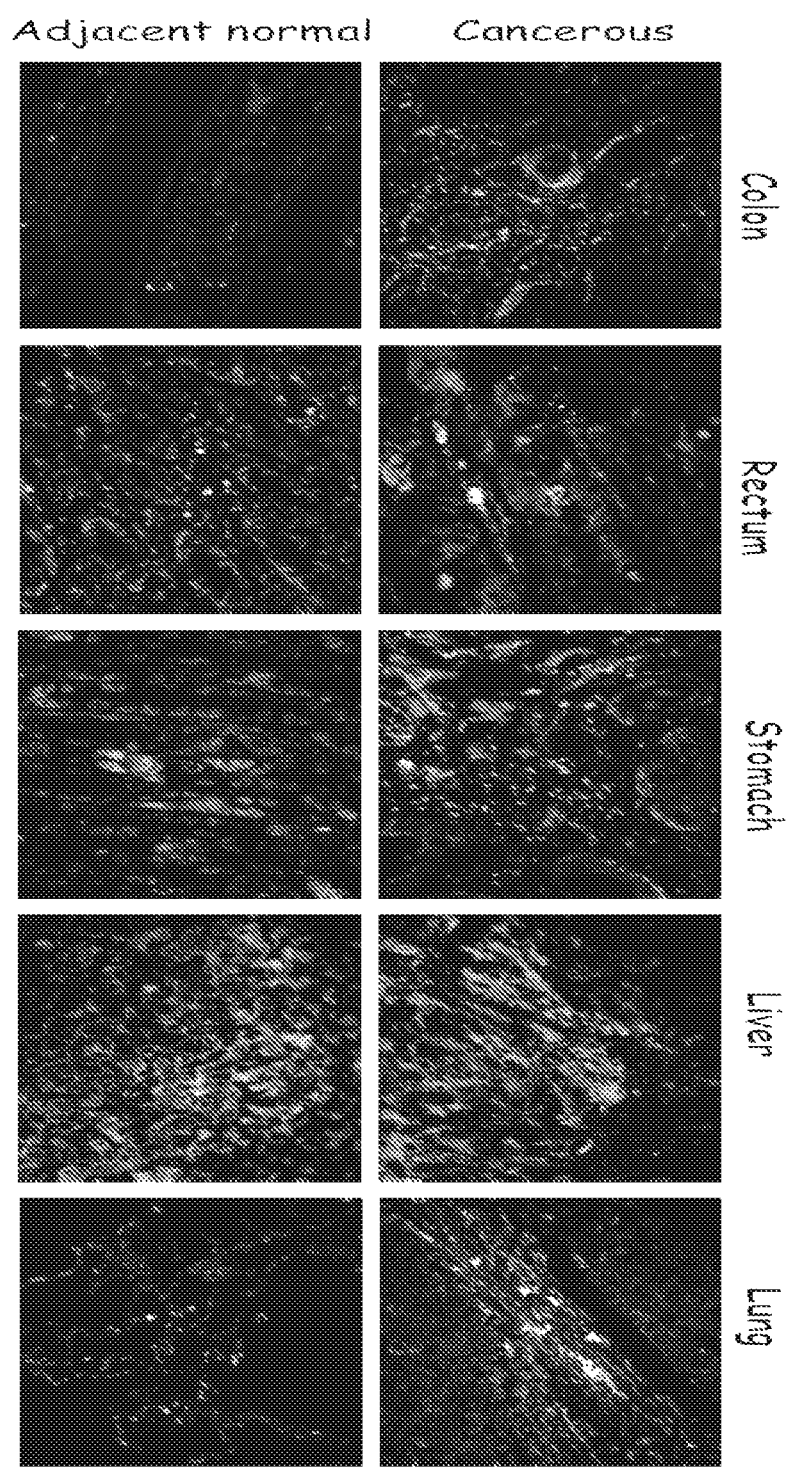
FIGS. 2A-2B are series of images depicting the detection of DKK2 proteins in histological sections of tumors of various tissue origins by immunohistostaining using the 5F8 Anti-DKK2 monoclonal antibody (mAb).
Figure 2B:
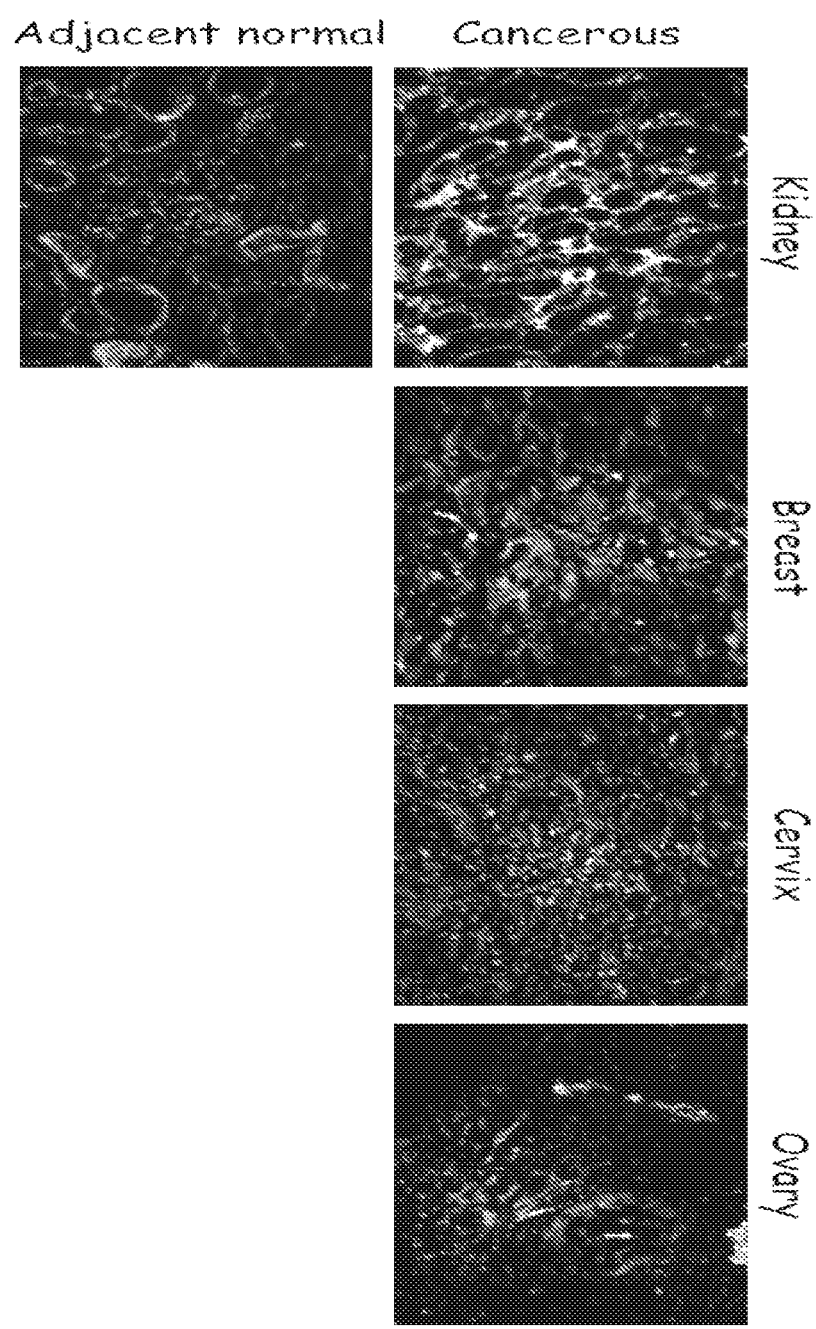

Analysis of publically available gene expression databases revealed that DKK2 is upregulated in many of the gastric-intestinal cancers, including rectal adenocarcinoma, colorectal carcinoma, gastric adenocarcinoma, and pancreatic ductal adenocarcinoma (FIG. 1). Immunohistostaining using anti-DKK2 antibody also revealed that DKK2 protein is upregulated in tumor samples from the colon, rectum, kidney, lung and stomach, and detected in tumor samples from the liver, breast, cervix and ovary (FIG. 2). These data suggest that DKK2 can be a relevant therapeutic target for treating human cancers.

Figure 3:
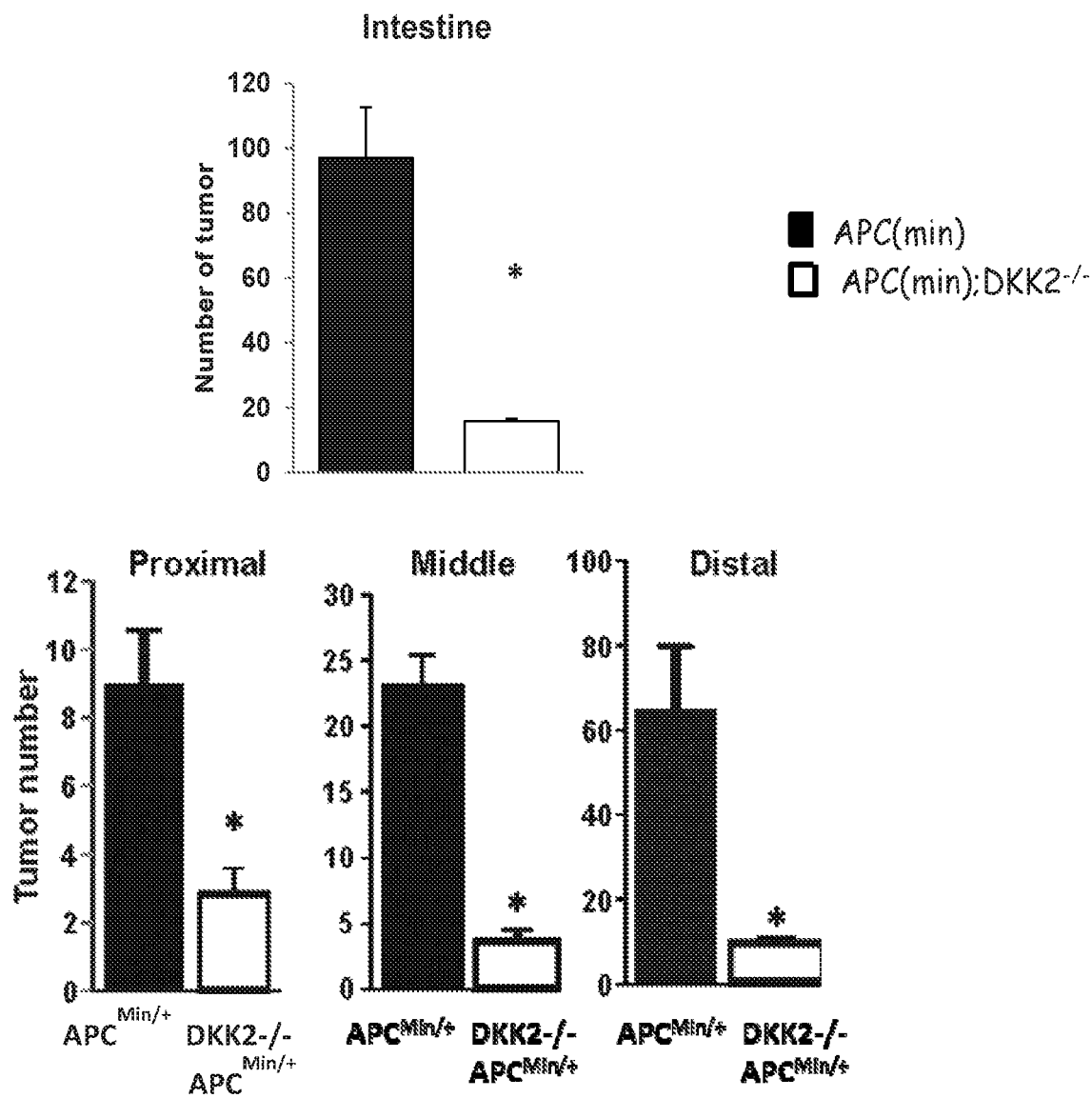
FIG. 3 is a series of histograms showing that genetic inactivation of DKK2 suppresses tumor progression in the APC(min) (aka, $APC^{min/+}$) mice, a mouse colon cancer model. n>10, *, p<0.01.
Figure 4:
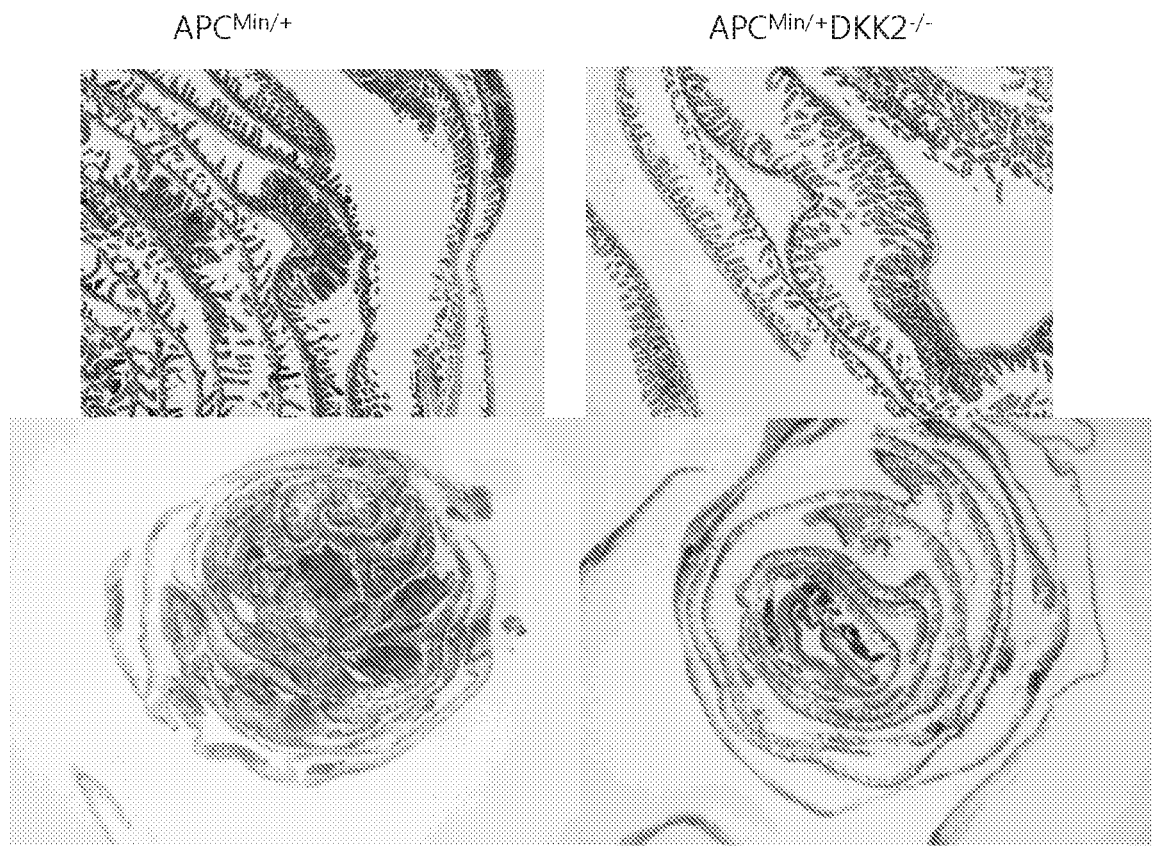
FIG. 4 is a series of images illustrating the decreased tumor burden in APCKO ($APC^{min/+}DKK2^{-/-}$) mice. These images showed that APCKO tumors tend to be smaller and less frequent than those of APC mice.

Example 2: Genetic DKK2 Deletion Leads to Reduced Tumor Burden in $APC^{Min/+}$ Mice APC (min) (also known as, $APC^{Min/+}$ mice) and APC (min); $DKK2^{-/-}$ mice were housed in a specific pathogen free vivarium. In the absence of DKK2, tumor progression was significantly reduced (FIG. 3 and FIG. 4). In accordance, tumor induced abnormalities such as splenomegaly, thymic atrophy and lymphopenia (You, S., et al., Int J Exp Pathol, 2006. 87(3): p. 227-36) were significantly lower in APCKO mice. This tumor reduction phenomenon was seen in groups of male and female mice on both high and low fat diets with consistent results. Together, these data strongly suggest that in the absence of DKK2, colon cancer progression is significantly lower.

Example 3: Generation of Anti-DKK2 Antibodies

Figure 5:
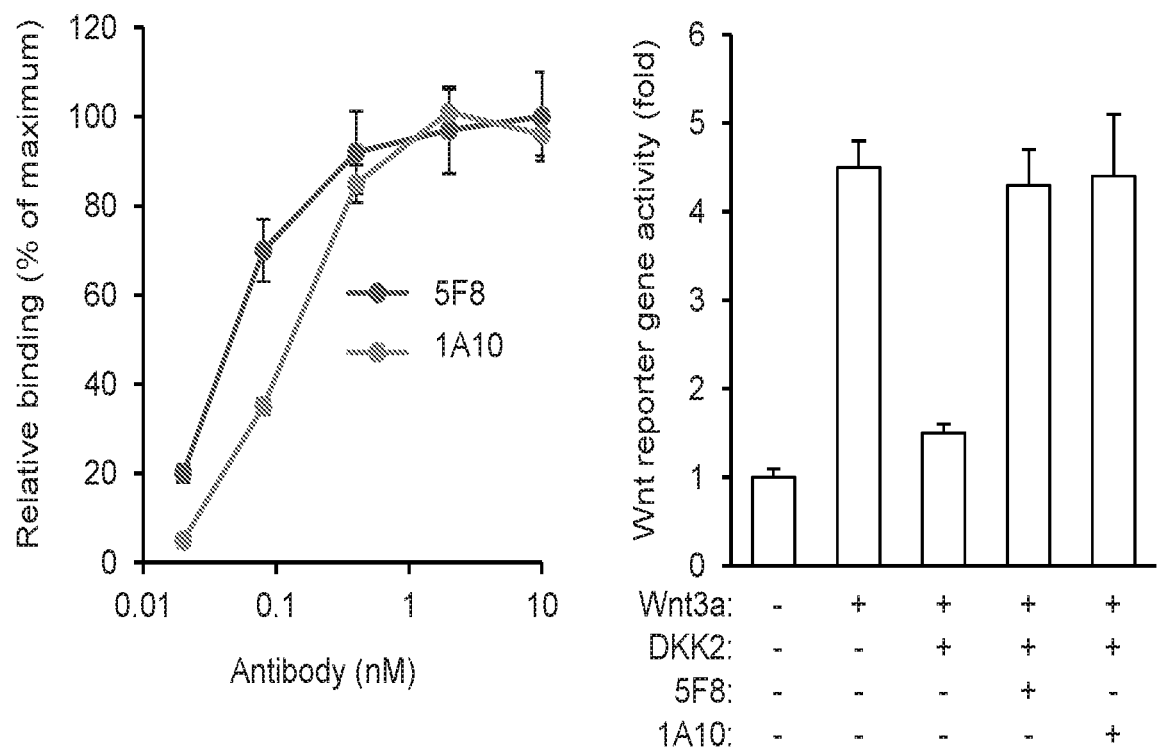
FIG. 5 is a series of graphs depicting the binding of mAb 5F8 and 1A10 antibody to the DKK2 protein and the ability of mAb 5F8 and 1A10 to reverse the inhibition of Wnt activity by DKK2 protein via a Wnt activity assay in HEK293 cells.
Figure 6:
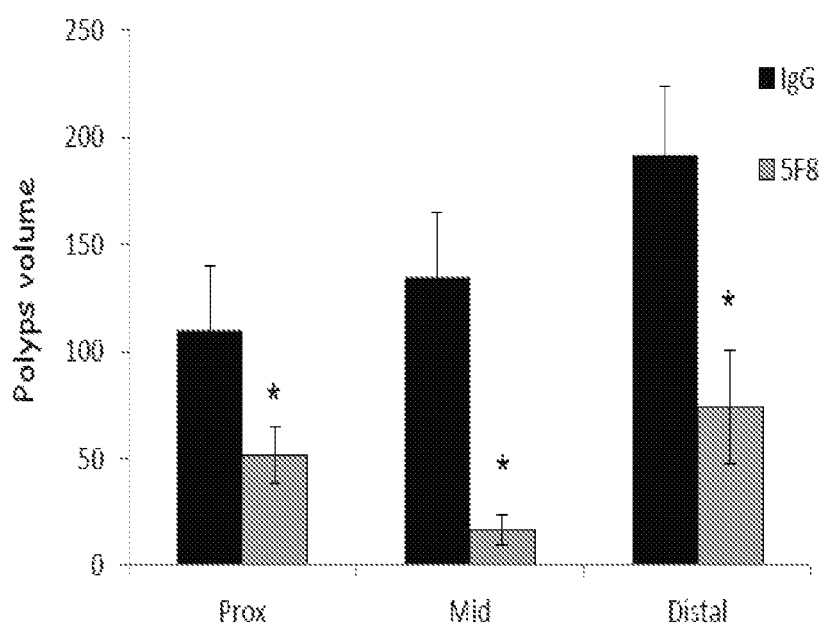
FIG. 6 is a histogram demonstrating the decrease in polyps volume in presence of the mAb 5F8 antibody in the APC(min) mice. APC(min) mice were treated with 150 μg mAb 5F8 twice a week for six weeks starting at the age of 10 weeks.
Figure 15:
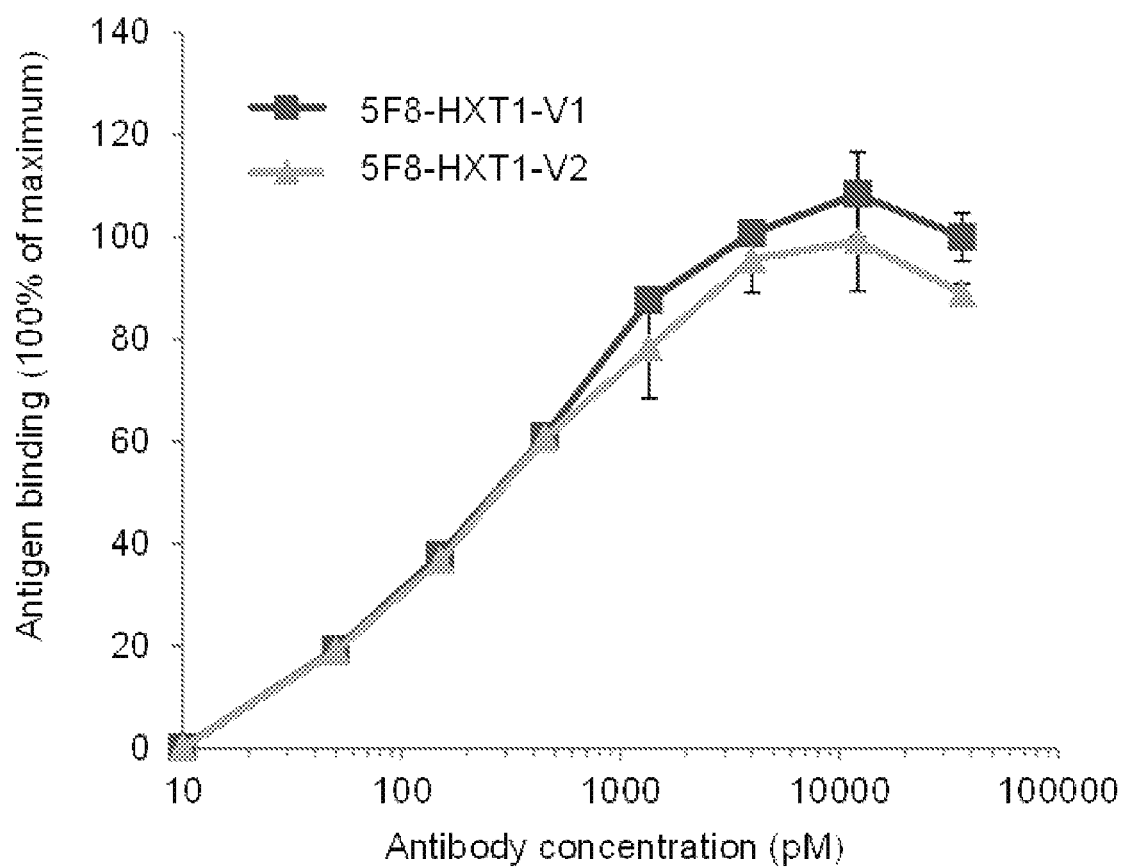
FIG. 15 is a graph demonstrating the binding of humanized anti-DKK2 antibodies to human DKK2 protein. Human DKK2 protein was coated on a ELISA plate and then incubated with the anti-DKK2 antibody followed by HRP-conjugated secondary antibody. The binding was determined using a chemiluminescence assay after the subtraction of background binding of the antibody to the plate.

DKK2 is secreted and is a suitable candidate to be targeted with an antibody (Ab) to reduce tumor burden. While DKK2 is important for eyelid development (Gage et al., Dev Biol, 2008. 317(1): p. 310-24), it is not known to have a vital function in adult mice. Two clones of mAb (5F8 and 1A10) were developed with high specificity for DKK2, which neutralize DKK2 and inhibit its Wnt antagonist functions (FIG. 5). Humanized antibodies carrying the same CDRs of 5F8 were generated, and two of them showed similar affinities for the DKK2 protein (FIG. 15).

Figure 9:
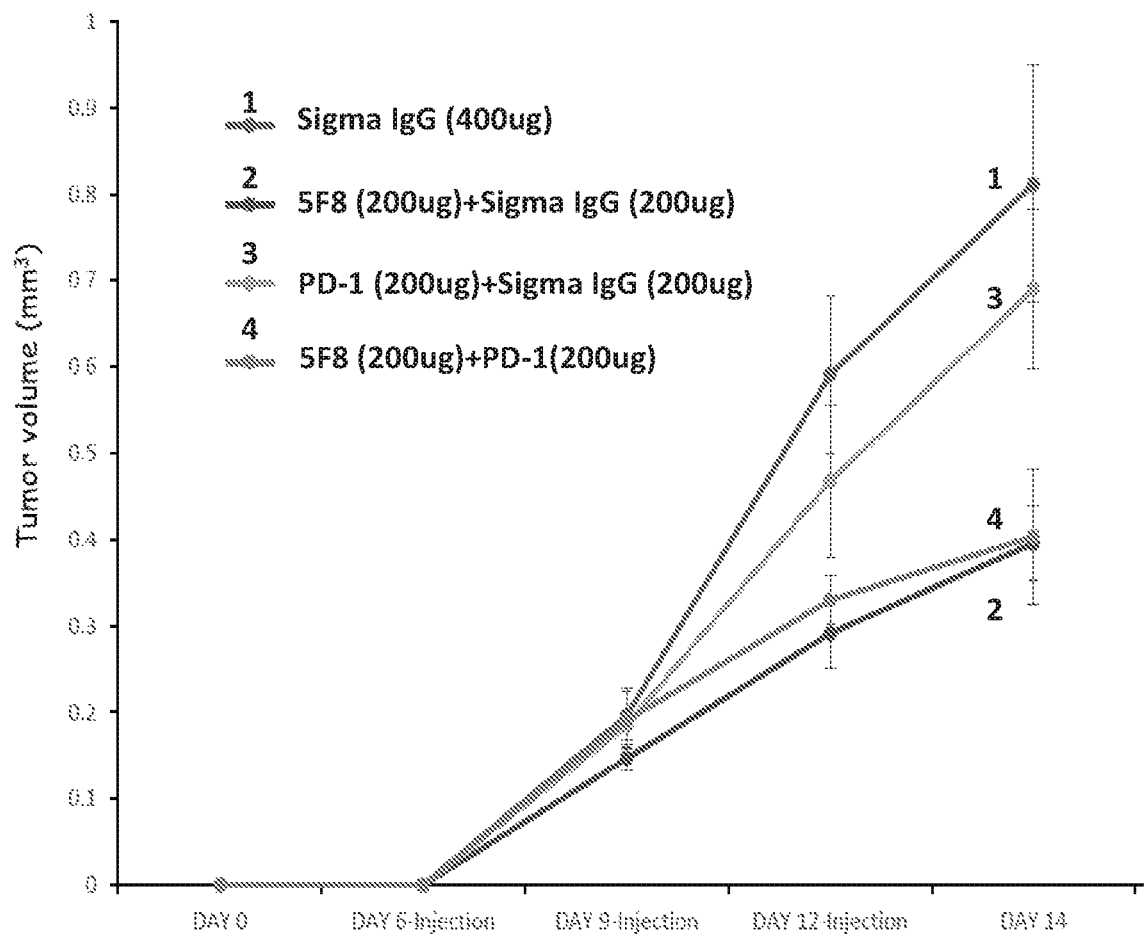
FIG. 9 is a graph depicting the suppressive effect of mAb 5F8 on allograft MC38 tumor growth in comparison to anti-PD-1. Immunocompetent C57Bl mice were grafted with tumor cells and mAb treatment started at Day 6, (n=5). The increases in tumor volume were plotted.
Figure 10:
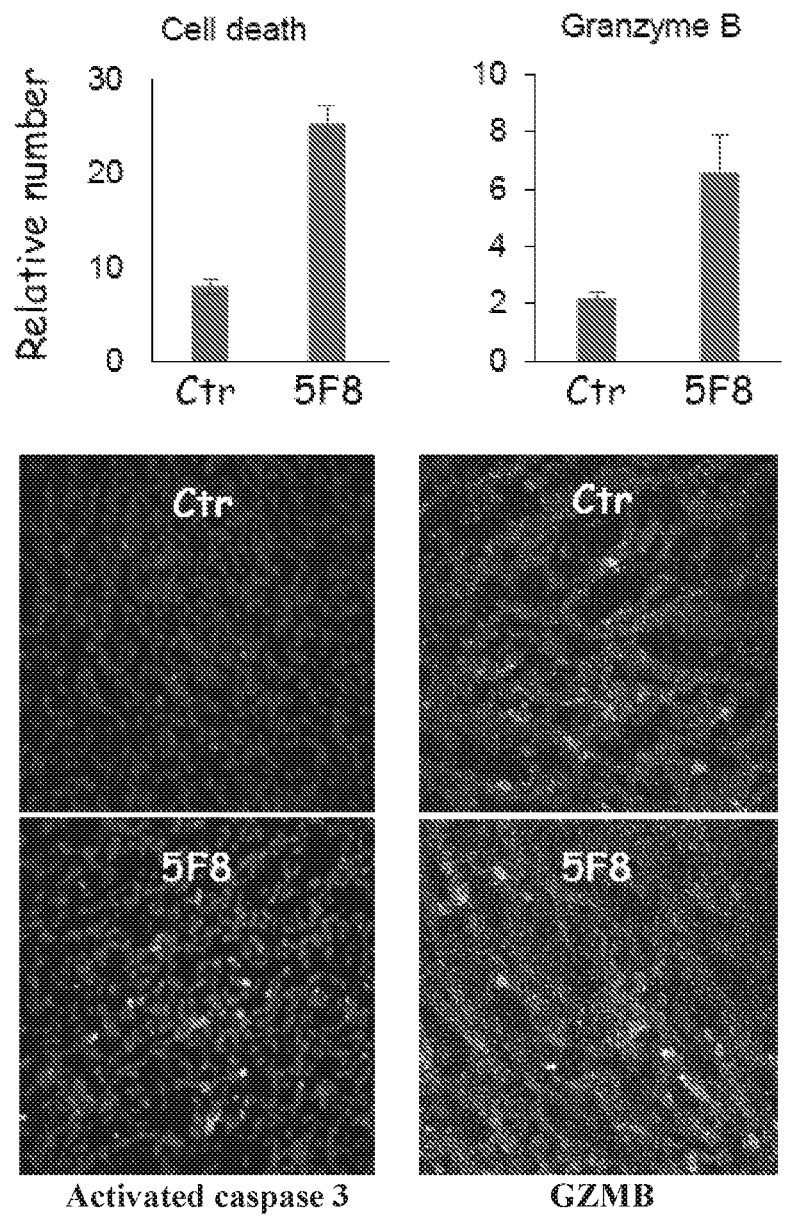
FIG. 10 is a series of histograms and images showing that mAb 5F8 neutralization reduces tumor burden accompanied by increases in Granzyme B-positive cells and tumor cell death in an allograft tumor model. Mouse colon cancer cells (MC38) were grafted subcutaneously to immunocompetent C57BL mice and treated with the anti-DKK2 mAb (5F8, also known as YAL-008-1-5F8) starting 6 days after engraftment. Tumor growth curves and immunostaining of tumor sections for apoptotic cells and Granzyme B positive cells are shown. n=5
Figure 11:
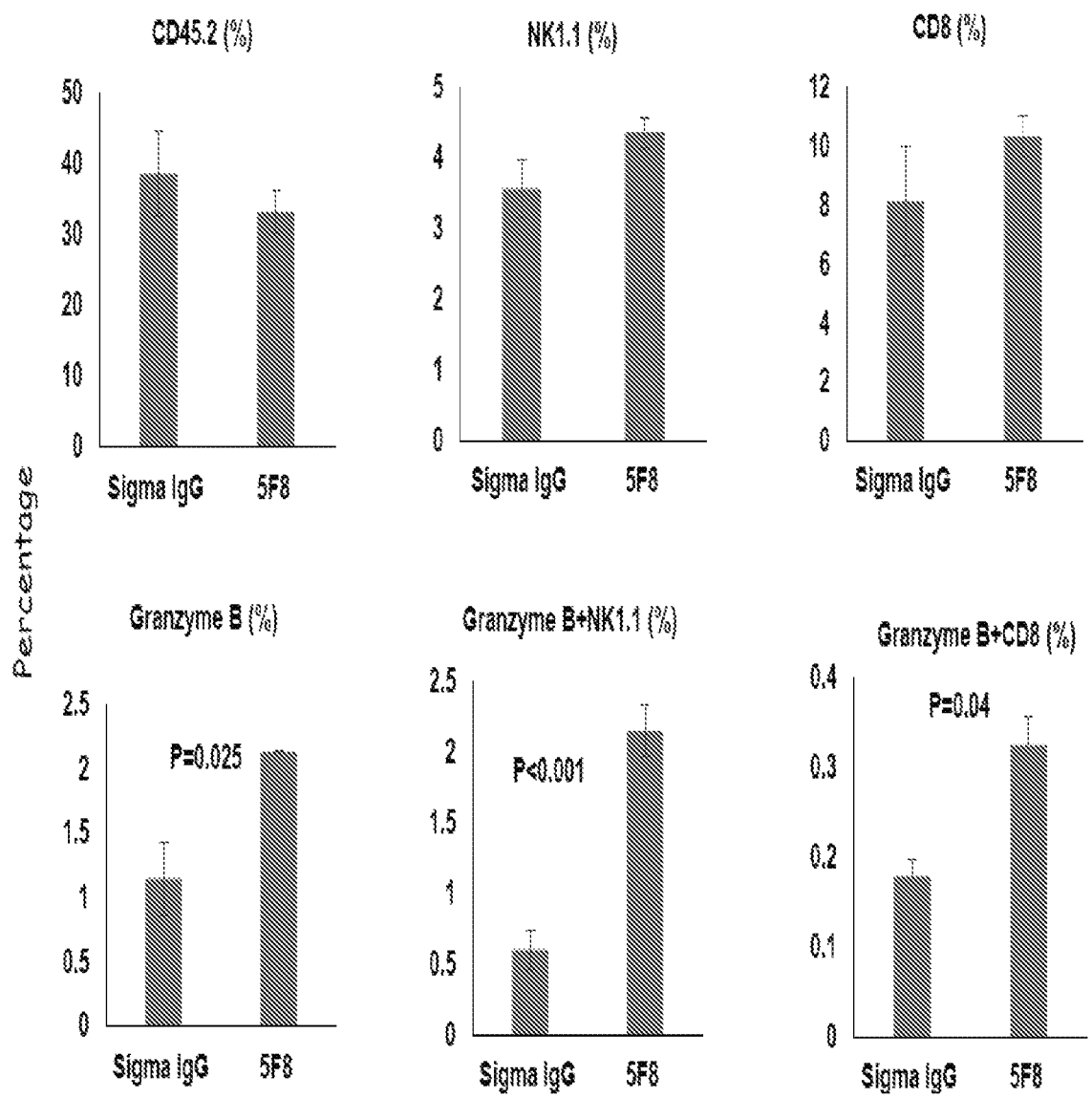
FIG. 11 is a series of histograms depicting that neutralizing anti-DKK2 antibody increases Granzyme B-positive NK and CD8 cells. Flow cytometry analysis of the cells in the allograft tumors revealed that DKK2 neutralization did not affect the number of CD45 hematopoietic cells, NK or $CD8^+$ cells, but increased the percentage of Granzyme B positive hematopoietic cells, NK and $CD8^+$ cells in the tumors. n=5

Example 4: Targeting DKK2 in a Graft Mouse Model of Colon Cancer Cells Showed that DKK2 is an Important Player for the Regulation of Tumor Behavior and Microenvironment MC38 cells, which were derived from mouse colon carcinoma in a C57BL mouse, progress very fast when grafted to immune-competent WT C57BL mice. Thus, this Xenograft model serves as a good alternative to aggressive advanced tumor models, which can be used to test the therapeutic potential of the anti-DKK2 Abs for treating advanced cancers. In one study, C57BL mice (n=5 per group) were grafted with MC38 cells. Six days later, the mice were treated via the intraperitoneal (IP) route with mouse IgG or mAb 5F8 at 8 mg/kg and mAb 5F8 showed a significant inhibition tumor growth (FIG. 9). Immunostaining of tumor sections revealed that mAb 5F8 increases tumor cell apoptosis and Granzyme B-positive cells (FIG. 10). Importantly, flow cytometry analysis of leukocytes infiltrated into these grafted tumors showed no differences in the number of CD45, NK, $CD8^+$, myeloid cells or CD4 but YAL008-1-5F8 treatment resulted in significant increases in Granzyme B-positive CD45-positive leukocytes including Granzyme B positive NK and $CD8^+$ cells (FIG. 11). These results suggest a mechanism that involves the regulation of effector immune cells in DKK2 neutralization-mediated suppression of tumor progression.

Figure 7:
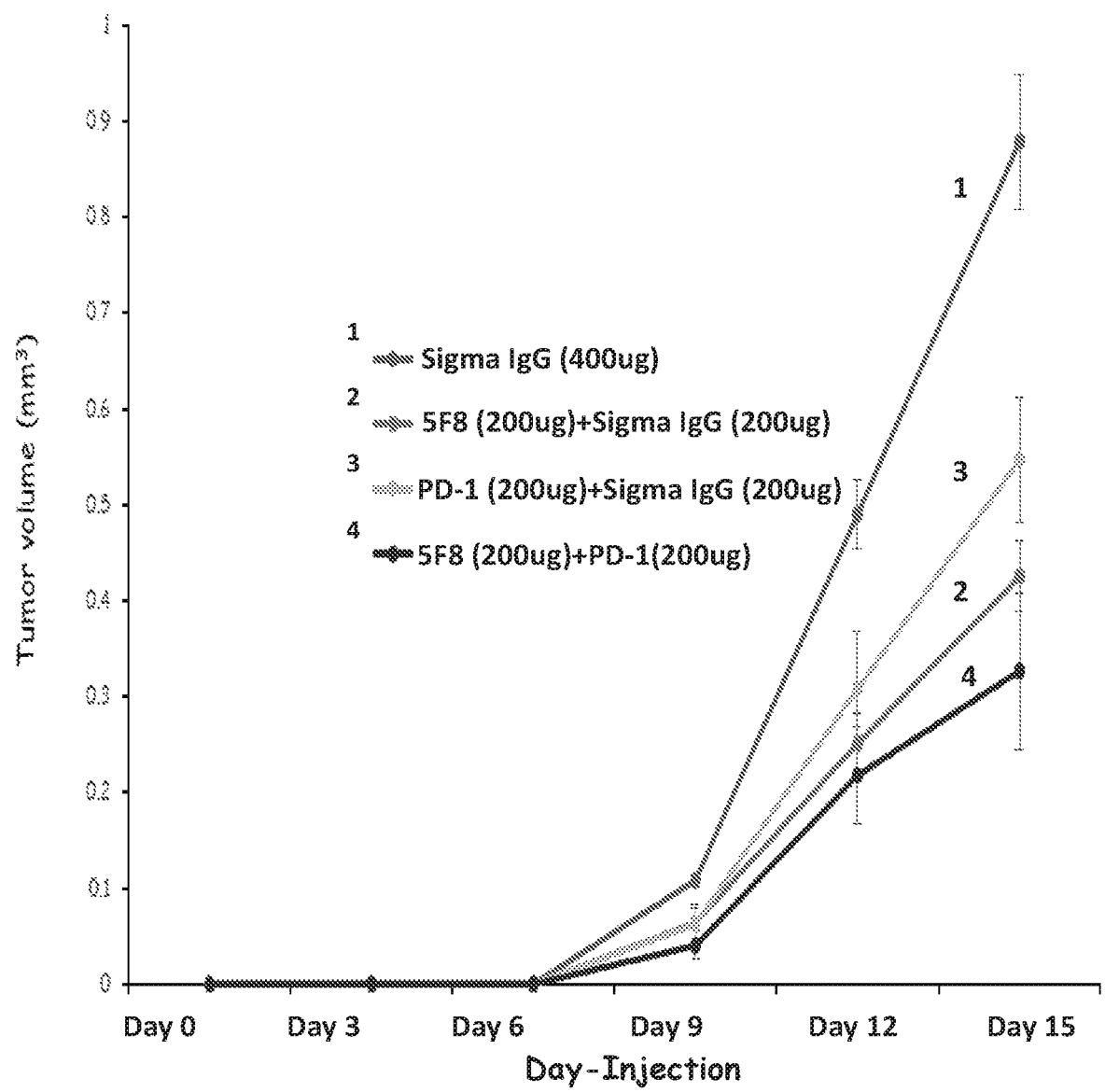
FIG. 7 is a graph depicting the suppressive effect of mAb 5F8 on allograft LLC tumor growth in comparison to anti-PD-1. Immunocompetent C57Bl mice were grafted with tumor cells and mAb treatment started at Day 3 (n=5).
Figure 8:
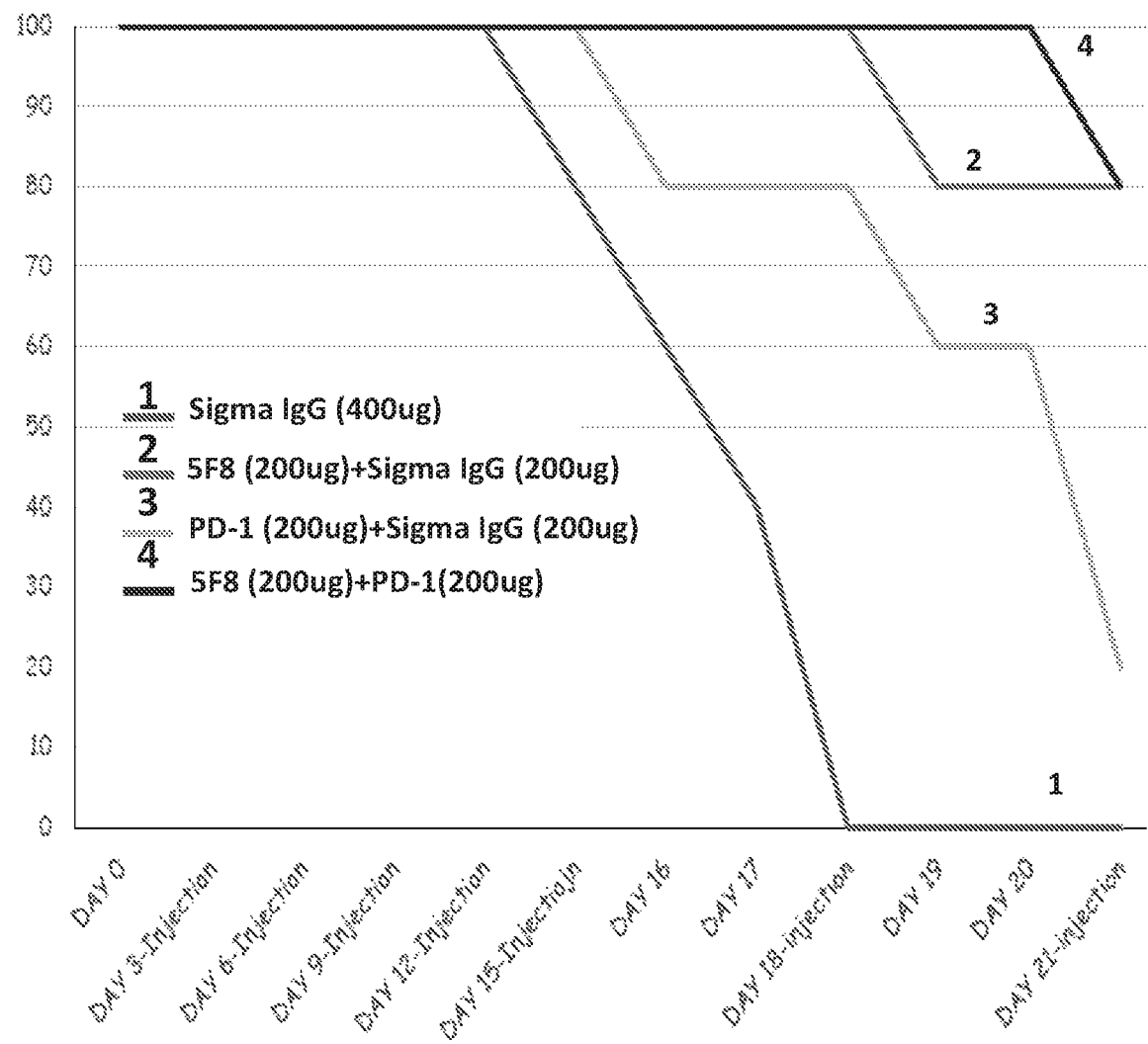
FIG. 8 is a graph depicting the effect of mAb 5F8 on the life extension of mice grafted with LLC tumor cells in comparison to anti-PD-1. The experiment was done similarly as in FIG. 7. Mice with tumor volume larger than 1.5 $CM^3$ were considered dead and euthanized.

Example 5: DKK2 Antibody Suppresses Lung Tumor Formation in an Allograft Model Mouse LLC lung cancer cells were grafted to C57BL mice and treated with anti-DKK2 antibody (YAL008-1-5F8). This antibody suppressed tumor formation (FIG. 7) and extended the survival of tumor-bearing mice (FIG. 8).

Example 6: Effect of DKK2 and Wnt on NK Cell Activation

Figure 17:
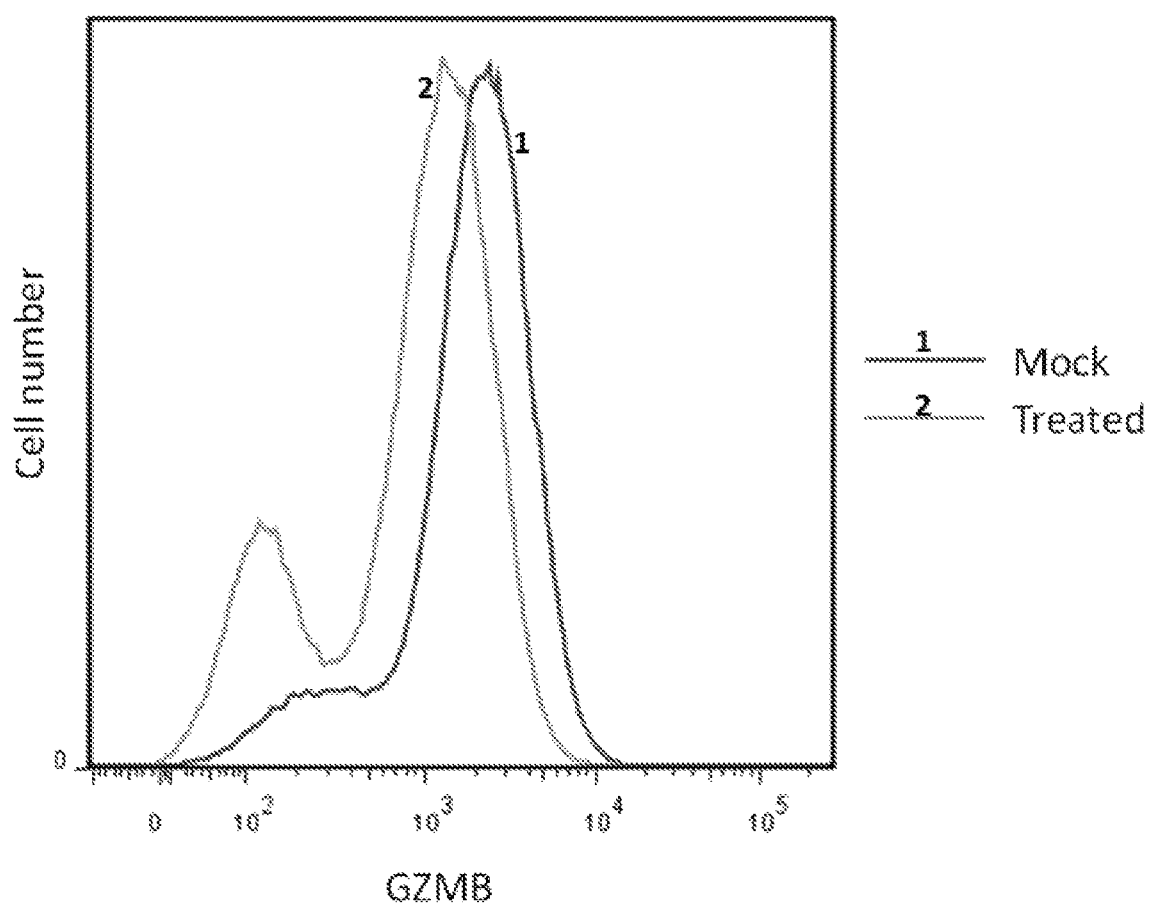
FIG. 17 is a graph demonstrating that DKK2 directly inhibited Granzyme B expression in a human NK cell line (NK92) together with Wnt5A. Recombinant Wnt5a and DKK2 (200 ng/ml) were added to NK-92MI cells for 24 hours and Granzyme B contents were analyzed by flow cytometry.

Human NK cell line NK-92 and primary mouse NK cells from spleens and MC38-grafted tumors were tested for their expression of Granzyme and cytotoxic activity in the presence or absence of recombinant proteins of DKK2, Wnt3a, Wnt5a and DKK1, and in the presence or absence of Wnt inhibitors (including LGK-974) and GSK inhibitors (including CHIR 99021). In this manner, the regulation of NK cell activation by DKK2 and Wnt was assessed. Experimental results showed that recombinant DKK2 and Wnt5a inhibited Granzyme B expression in human NK92 cells (FIG. 17), suggesting that DKK2 may be directly involved in the inhibition of immune effector cells.

Figure 14:
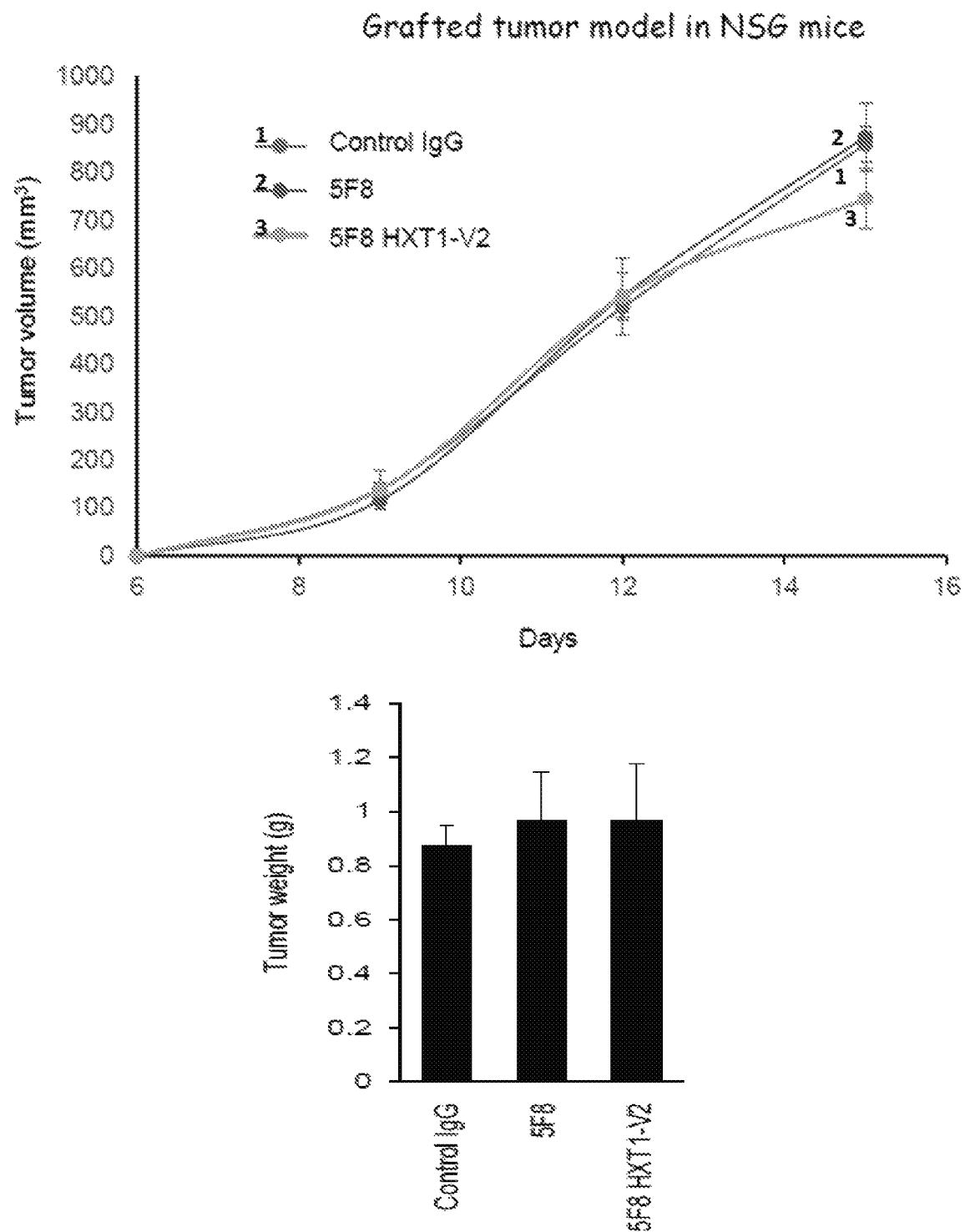
FIG. 14 is a series of graph and histogram showing that the suppressive effect of mouse anti-DKK2 antibody Y008-1-5F8 or its humanized antibody 5F8-HXT1-V2 on grafted MC38 tumor progression is dependent on the host immunity. These antibodies failed to show significantly suppressive effect on the tumor progression in MC38-grafted immunodeficient NSG mice purchased from JAX.

Example 7: Anti-DKK2 Antibodies Inhibit Tumor Formation in an Immune-Dependent Manner When MC38 cells were grafted to immunodeficient NSG mice, which lack mature B and T lymphocytes, myeloid cells, and NK cells, neither mAb 5F8 nor humanized 5F8 showed any suppressive effect on tumor growth (FIG. 14). These results indicate DKK2 neutralization inhibit tumor formation depending on the presence of host immunity.

Example 8: Anti-DKK2 Antibody Optimally Suppresses Tumor Formation when Associated with PD-1 Antibody C57BL mice (n=5 per group) were grafted with LLC or MC38 cells. Days later, the mice were treated via the intraperitoneal (IP) route with mouse IgG, an anti-DKK2 antibody (5F8) and/or anti-mouse PD-1 antibody at 16 mg (8 mg per antibody)/kg. The effect of mAb 5F8 on tumors formation was compared with a PD-1 antibody (Cancer Res. 2005 Feb. 1; 65(3):1089-96). In the LLC allograft lung tumor model, mAb 5F8 had a similar effect on tumor retardation as did PD-1 antibody, and the combination of mAb 5F8 and PD-1 antibody exhibited a greater suppression of tumor progression than with PD-1 antibody alone (FIG. 7); 5F8 and the combination of 5F8 and PD-1 antibody exhibited increased survival compared to the use of PD-1 antibody alone (FIG. 8). FIG. 9 illustrates the comparative effect of mAb 5F8 on tumor formation when administered alone or in combination with other antibodies in the MC38 colon cancer model. In this MC38 model, PD-1 antibody did not exhibit a significant effect on tumor formation.

Figure 12:
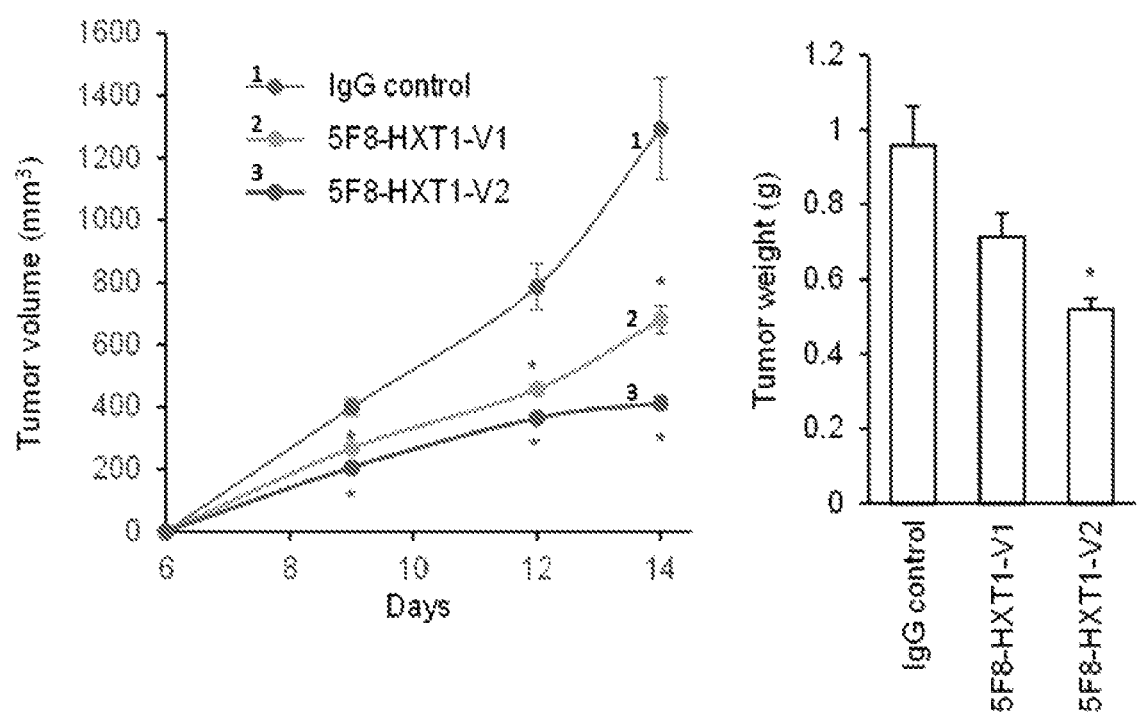
FIG. 12 is a series of graph and histogram depicting the effect of humanized anti-DKK2 antibodies on tumor progression in an allograft model. MC38 cells were inoculated to C57BL mice (8 weeks old) and treated with the antibodies at Days 6, 9 and 12 (200 μg/treatment). The antibodies showed significant inhibition of tumor growth. *, p<0.05 vs. control IgG (n=5, Student's t-Test). Tumors were analyzed by flow cytometry.

Example 9: Humanized Anti-DKK2 Antibody can Significantly Inhibit Tumor Growth Humanized anti-DKK2 antibodies 5F8-HXT1-V1 and 5F8-HXT1-V2, were prepared and shown to bind with a very high affinity to human DKK2 protein (FIG. 15). Both antibodies showed a significant inhibition of tumor growth in an allograft model (MC38 cells) (FIG. 12). FIG. 13 demonstrated that 5F5-HXT1-V2 treatment increased Granzyme B-positive immune cells, including CD8 positive lymphocytes and NK1.1 positive neutral killer cells.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A pharmaceutical composition comprising a humanized anti-Dickkopf2 (anti-DKK2) antibody or fragment thereof and a pharmaceutical acceptable carrier; wherein the humanized anti-DKK2 antibody comprises SEQ ID NO: 2 and at least one of the amino acid sequences selected from the group consisting of SEQ ID NOs: 1 and 3.

2. The pharmaceutical composition of claim 1, wherein the humanized anti-DKK2 antibody possesses neutralizing activity.

3. The pharmaceutical composition of claim 1, wherein the humanized anti-DKK2 antibody targets a DKK2 neutralizing epitope that comprises the amino acid sequence SEQ ID NO: 5.

4. The pharmaceutical composition of claim 1, comprising an additional agent selected from the group consisting of a chemotherapeutic agent, an anti-cell proliferation agent, an immunotherapeutic agent and any combination thereof.

5. The pharmaceutical composition of claim 1, wherein the additional agent is a programmed cell death 1 (PD-1) antibody.

6. A kit for diagnosing a cancer or a predisposition for developing a cancer or a metastasis in a subject, the kit comprising a humanized anti-DKK2 antibody targeting a DKK2 epitope comprising the amino acid sequence SEQ ID NO: 5; wherein the humanized anti-DKK2 antibody comprises SEQ ID NO: 2 and at least one of the amino acid sequences selected from the group consisting of SEQ ID NOs: 1 and 3.

* * * * *